United States Patent [19]

Tobia et al.

[11] Patent Number: 5,303,698
[45] Date of Patent: Apr. 19, 1994

[54] MEDICAL VENTILATOR

[75] Inventors: Ronald L. Tobia, Aberdeen; Russell J. Fischer, North Plainfield; Robert T. Chilcoat, Bridgewater, all of N.J.

[73] Assignee: The BOC Group, Inc., New Providence, N.J.

[21] Appl. No.: 750,850

[22] Filed: Aug. 27, 1991

[51] Int. Cl.$^5$ .............................................. A61M 16/00
[52] U.S. Cl. ........................... 128/204.21; 128/204.25; 128/205.24
[58] Field of Search .................. 128/204.21, 204.18, 128/204.25, 204.22, 205.11, 205.13, 205.18, 203.25, 205.24

[56] References Cited

U.S. PATENT DOCUMENTS

| | | | |
|---|---|---|---|
| 3,741,208 | 6/1973 | Jonsson | 128/204.21 X |
| 4,001,700 | 1/1977 | Cook | 128/204.21 X |
| 4,036,221 | 7/1977 | Hillsman | 128/204.23 |
| 4,393,869 | 7/1983 | Boyarsky et al. | 128/204.18 |
| 4,448,192 | 5/1984 | Stawitcke et al. | 128/204.26 |
| 4,457,304 | 7/1984 | Molnar | 128/204.25 |
| 4,459,982 | 7/1984 | Fry | 128/204.23 |
| 4,520,812 | 6/1985 | Freitag | 128/204.25 |
| 4,533,346 | 8/1985 | Cosgrove | 604/66 |
| 4,602,653 | 7/1986 | Ruiz-Vela | 137/88 |
| 4,766,894 | 8/1988 | Legrand | 128/204.21 |
| 4,838,257 | 6/1989 | Hatch | 128/204.18 |
| 4,838,259 | 6/1989 | Gluck | 128/201.21 |
| 4,971,049 | 11/1990 | Rotario | 128/204.21 |
| 5,072,729 | 12/1991 | Devries | 128/204.23 |
| 5,072,737 | 12/1991 | Goulding | 128/718 |
| 5,092,326 | 3/1992 | Winn | 128/205.13 |
| 5,107,830 | 4/1992 | Younes | 128/204.18 |
| 5,183,038 | 2/1993 | Hoffman | 128/204.21 |

Primary Examiner—Edgar S. Burr
Assistant Examiner—Eric P. Raciti
Attorney, Agent, or Firm—Roger M. Rathbun; Larry R. Cassett; Arnold Dompieri

[57] ABSTRACT

A medical ventilator is provided for providing continuous, closed-loop control of the pressure of gas within a patient's mouth or respiratory tract in accordance with any selected pressure input waveform. The medical ventilator comprises an adaptive, feedback controller which provides independent control of the inspiratory and expiratory branches of the ventilator, while continuously controlling mouth pressure. The digital coefficients of the controller are updated to adjust for variations in the resistance of the patient's respiratory tract resulting from the magnitude of flow of inspiratory gas into the tract and patient-to-patient differences. Pressure in the expiratory branch is controlled by controlling, through a pressure-regulating valve, the magnitude of back pressure applied to a diaphragm valve. A venturi provides a reference pressure for the pressure-regulating valve below that of the surrounding atmosphere to enable application of a negative back pressure to the diaphragm valve.

59 Claims, 13 Drawing Sheets

MEDICAL VENTILATOR

BACKGROUND OF THE INVENTION

This invention pertains to apparatus and methods for medical ventilation and, more particularly, to apparatus and methods for controlling the pressure of gases within a patient's mouth or respiratory tract during medical ventilation.

There are a number of ventilatory techniques or ventilatory modes used by physicians to assist a patient's respiratory function and to reabilitate his or her respiratory capacity. These techniques or modes include positive end-expiratory pressure (PEEP), intermittent mandatory ventilation (IMV), continuous positive airway pressure (CPAP), intermittent positive pressure breathing (IPPB), high-frequency ventilation (HFV) and others. Since the optimum pressure, flow and gas-volume characteristics differ for each of these techniques or modes and, for any given mode, from patient to patient, a medical ventilator designed to perform optimally in one of these modes and for a particular type of patient is unlikely to perform optimally in other modes and for other types of patients. A medical ventilator capable of continuous, high speed control of the pressure of gases within a patient's mouth in accordance with any selected pressure waveform and for any patient's respiratory characteristics, however, could optimally perform all of these ventilatory modes with a minimum of patient-effort and with a high degree of patient-comfort. Such a ventilator also could enable the development of entirely new ventilatory techniques. No such medical ventilator presently exists.

U.S. Pat. No. 4,838,257 to Hatch discloses a medical ventilator with pressure and flow monitors located at various points within the pneumatic circuit for providing feedback to a computer-controller. Hatch states that his system enables one to "select the desired frequency, volume, pressure, phase relationships and waveform of gases being used to ventilate the lungs of a patient." column 6, lines 11-14. Other than showing the use of a computer-controller and the provision of feedback signals, however, Hatch provides little teaching on how to accomplish these goals.

U.S. Pat. No. 4,448,192 to Stawitcke et al. discloses a medical ventilator intended to follow a selected pressure-volume waveform. A controller compares pressure and gas-volume feedback signals, provided from piston-driven pumps, with a desired pressure-volume waveform and generates a pressure-error signal for controlling the pumps. Although Stawitcke et al. also shows the use of feedback to a controller, this reference also provides little teaching on how to control the actual pressure of gas within a pneumatic circuit, particularly the actual pressure within, or closely adjacent to, a patient's mouth or respiratory tract, in accordance with any selected pressure waveform.

U.S. Pat. No. 4,393,869 to Boyarsky et al. discloses a medical ventilator with an electrical controller and an electrical-to-pneumatic transducer "for controlling the pressure of . . . regulated air in accordance with a predetermined electrical signal." column 8, lines 2-4. The Boyarsky et al. feedback system is not a closed loop, however, and, therefore, does not attempt to cause the actual pressure within the pneumatic circuit to follow a pressure represented by the electrical signal or any other desired pressure. Also, although Boyarsky et al. discloses a pressure detector for providing feedback signals to the controller, these signals are used only to monitor the "duration of inspiration and expiration" and to insure closure of an expiratory valve at a time when "a residual pressure [remains] in the lungs," not to provide closed-loop control. column 9, lines 30-31, 34.

SUMMARY OF THE INVENTION

The present invention provides apparatus and methods for providing continuous, closed-loop control of the pressure of gases within the pneumatic circuit of a medical ventilator, particularly within, or closely adjacent to, a patient's mouth or respiratory tract, in accordance with any selected pressure waveform. The phrase "closed-loop control," as used herein, means the control of a parameter, in this case the control of the pressure of gas within, or closely adjacent to, a patient's mouth or respiratory tract, by a controller which responds to deviations between the parameter's actual value and its desired value.

One aspect of the present invention provides a medical ventilator comprising a source of inspiratory gas, an inspiratory conduit for directing the flow of the inspiratory gas from the source to a patient's mouth, and an inspiratory flow-control means for controlling the flow of the inspiratory gas within the inspiratory conduit. Means, e.g., a piezoresistive pressure sensor on the patient's wye piece, are provided for measuring the actual pressure of gas at a location indicative of that within the patient's mouth or respiratory tract. A comparator is provided for comparing the actual pressure with a desired pressure and for generating a first error signal indicative of the difference between the actual pressure and the desired pressure. A processor also is provided for processing this error signal and for generating a first control-signal for controlling the inspiratory flow-control means such that the actual pressure tracks the desired pressure. Preferably, the comparator and processor are effected by a digital microprocessor.

In accordance with this aspect of the invention, the processor executes an inspiratory control function having a time constant, and means are provided for updating the value of this time constant. Since the pneumatic circuit includes the patient and his or her respiratory tract (mouth, trachea, bronchial tubes, lungs, etc.) the accurate control of gas pressure within the patient's mouth and/or respiratory tract preferably includes updating of this time constant.

The value of the inspiratory control function's time constant is a function of the resistance ($R_p$) and compliance ($C_p$) of the patient's respiratory tract. These values vary from patient to patient and, more particularly, the value of $R_p$ varies as a function of the magnitude of flow of gas into the patient's respiratory tract. The time-constant updating means, therefore, preferably includes means for changing the value of the inspiratory time constant as a function of the flow of gas into the patient's respiratory tract. In the alternative, since the magnitude of this flow is directly related to the magnitude of the control signal controlling the inspiratory flow-control means, the value of this time constant may be adjusted as a function of the magnitude of this control signal. These adjustments compensate for flow-induced variations in $R_p$. In addition, the time-constant updating means preferably includes means for changing the value of the inspiratory time constant as a function of variations in the values of $R_p$ and $C_p$ from patient to patient (patient-induced variations). Good results can be achieved, however, by selecting a nominal value for $C_p$ and adjusting for flow-induced and patient-induced variations in $R_p$ only.

The medical ventilator, in accordance with the present invention, preferably also includes means for continuously controlling the proportion of oxygen within the total flow of inspiratory gas within the inspiratory conduit. In accordance with this aspect of the invention, the source of inspiratory gas includes a source of oxygen and a source of air, and the inspiratory flow-control means includes a first valve for controlling the flow of oxygen and a second valve for controlling the flow of air. Means are provided for measuring the actual flow of oxygen through the first valve, the actual flow of air through the second valve, and for determining the actual proportion of one of these flows to the total of both flows. A second comparator, preferably also effected by the processor, also is provided for comparing the actual proportion with a desired proportion and for generating a second error signal indicative of the difference between the actual proportion and the desired proportion. The processor further includes means for processing this second error signal and for generating the first control signal such that the actual proportion tracks the desired portion.

The processor preferably is a digital microprocessor which processes the error signals in accordance with a set of digital coefficients, and the time-constant updating means preferably comprises means, within the processor, for changing the value of these digital coefficients in accordance with the measurements of flow-induced and patient-induced variations in $R_p$ and $C_p$. The digital output from the microprocessor preferably is converted to an analog signal for controlling the inspiratory flow-control means.

A further aspect of the present invention is the provision of an expiratory conduit for directing the flow of expiratory gas from the patient's mouth, and an expiratory flow-control means for controlling the pressure of the expiratory gas. In accordance with this aspect of the invention, the processor includes means for generating a second control signal, in response to the first error signal, for controlling the expiratory flow-control means such that the actual pressure of gas within the patient's mouth or respiratory tract tracks the desired pressure. The processor preferably executes an independent expiratory control function for controlling the expiratory flow-control means.

The expiratory flow-control means preferably includes a diaphragm valve and a pressure-regulating valve for applying back pressure to the diaphragm valve. The pressure-regulating valve may include means, such as a venturi, for applying a negative back pressure to the diaphragm valve. The application of a negative back pressure lowers the non-linear, saturation threshold of the pressure-regulating valve, enabling a higher speed of response, and reduces expiratory resistance, particularly at pressures close to that of the surrounding atmosphere. The means for applying a negative back pressure preferably also includes means for opening the diaphragm valve in the event of an electrical failure, insuring an unobstructed airway between the patient's mouth and the atmosphere.

The expiratory conduit may also include, downstream from the diaphragm valve, means for creating a pressure below that of the surrounding atmosphere. Such means also lowers the non-linear, saturation threshold of the pressure-regulating valve and, because of the apparatus' ability to precisely control mouth pressure, the application of negative pressure poses no risk to patient-safety.

A further aspect of the present invention is the provision of synchronization means for synchronizing the inspiratory and expiratory flow-control means such that the effect of each is exclusive and mouth pressure is continuously controlled. In accordance with this aspect of the invention, evaluating means are provided for evaluating, throughout the course of the patient's respiratory cycle, the capacity of the first control signal and the inspiratory means, and the capacity of the second control signal and the expiratory means, for causing actual pressure to track desired pressure. Selecting means are provided for selecting, on the basis of this evaluating, either the first control signal and the inspiratory means, or the second control signal and the expiratory means, for controlling actual pressure. Preferably, the evaluating and selecting means also are effected by the processor.

The synchronization means preferably includes means for setting the first control signal to a predetermined value during periods when the inspiratory means lacks the capacity for causing actual pressure to track desired pressure, and for setting the second control signal to a predetermined value (although not constant) during periods when the expiratory means lacks the capacity for causing actual pressure to track desired pressure. These predetermined values preferably prohibit the inspiratory and expiratory means, when not controlling actual pressure, from transmitting inspiratory and expiratory gas, respectively, and provide for the immediate seizure of control by the expiratory means for the venting of over pressures (such as a cough). If the expiratory means comprises a diaphragm valve and a pressure-regulating valve, the second control signal's predetermined value preferably causes the pressure-regulating valve to apply a back pressure equal to a predetermined incremental pressure plus the desired pressure. Since this expiratory sealing pressure closely tracks the desired mouth pressure, any over pressure is quickly vented to the atmosphere and a smooth transition occurs between inspiratory and expiratory control. A medical ventilator in accordance with this aspect of the invention achieves a high degree of patient-comfort such as, e.g., during spontaneous inspiration or expiration. The controller switches between inspiratory and expiratory control quickly and comfortably, while continuously causing actual pressure to track desired pressure.

In order to more precisely control the back pressure applied to the diaphragm valve, the present invention preferably also includes a second closed loop controller for controlling this pressure. In accordance with this aspect of the invention, means are provided for measuring the actual back pressure applied to the diaphragm valve. A third comparator is provided for comparing the pressure represented by the second control signal with this actual back pressure and for generating a third error signal indicative of the difference between the actual back pressure and this pressure. The controller processes this third error signal in accordance with a third set of processing parameters and generates a third control signal for controlling the means for applying back pressure to the diaphragm valve such that the actual pressure tracks the desired back pressure. The controller and third comparator also preferably are part of the processor.

Further aspects of the present invention provide a method for controlling the pressure of gas within a patient's mouth or respiratory tract. This method includes providing a source of inspiratory gas, directing a flow of the inspiratory gas from the source to the patient's mouth, measuring the actual pressure of gas at a location indicative of that within the patient's mouth or respiratory tract, comparing the actual pressure with a desired pressure and generating an error signal indicative of the difference between the actual pressure and the desired pressure. This method further includes processing the error signal in accordance with a set of processing parameters and generating a control signal for controlling the flow of inspiratory gas such that the actual pressure tracks the desired pressure. The method preferably also includes adjusting the values of the processing parameters as a function of the flow of inspiratory gas into the patient's mouth or the value of the control signal. These processing parameters preferably also are adjusted as a function of the flow-induced and patient-induced variations in the resistance and compliance of the patient's respiratory tract.

The method preferably also includes directing expiratory gas from the mouth of the patient, processing the error signal in accordance with a second set of processing parameters and generating a second control signal for controlling the pressure of expiratory gas. An evaluation preferably also is made of the capacity of the first control signal and the directing of inspiratory gas, and the capacity of the second control signal and the directing of expiratory gas, for causing the actual pressure to track the desired pressure. Finally, the method preferably includes selecting, on the basis of this evaluating, either the first control signal and the directing of inspiratory gas, or the second control signal and the directing of expiratory gas, for controlling the actual pressure.

Other objects, features and advantages of the present invention will be more readily apparent from the detailed description of the preferred embodiments set forth below, taken in conjunction with the accompanying drawings.

DETAILED DESCRIPTION OF THE PREFERRED EMBODIMENTS

Figure 1:
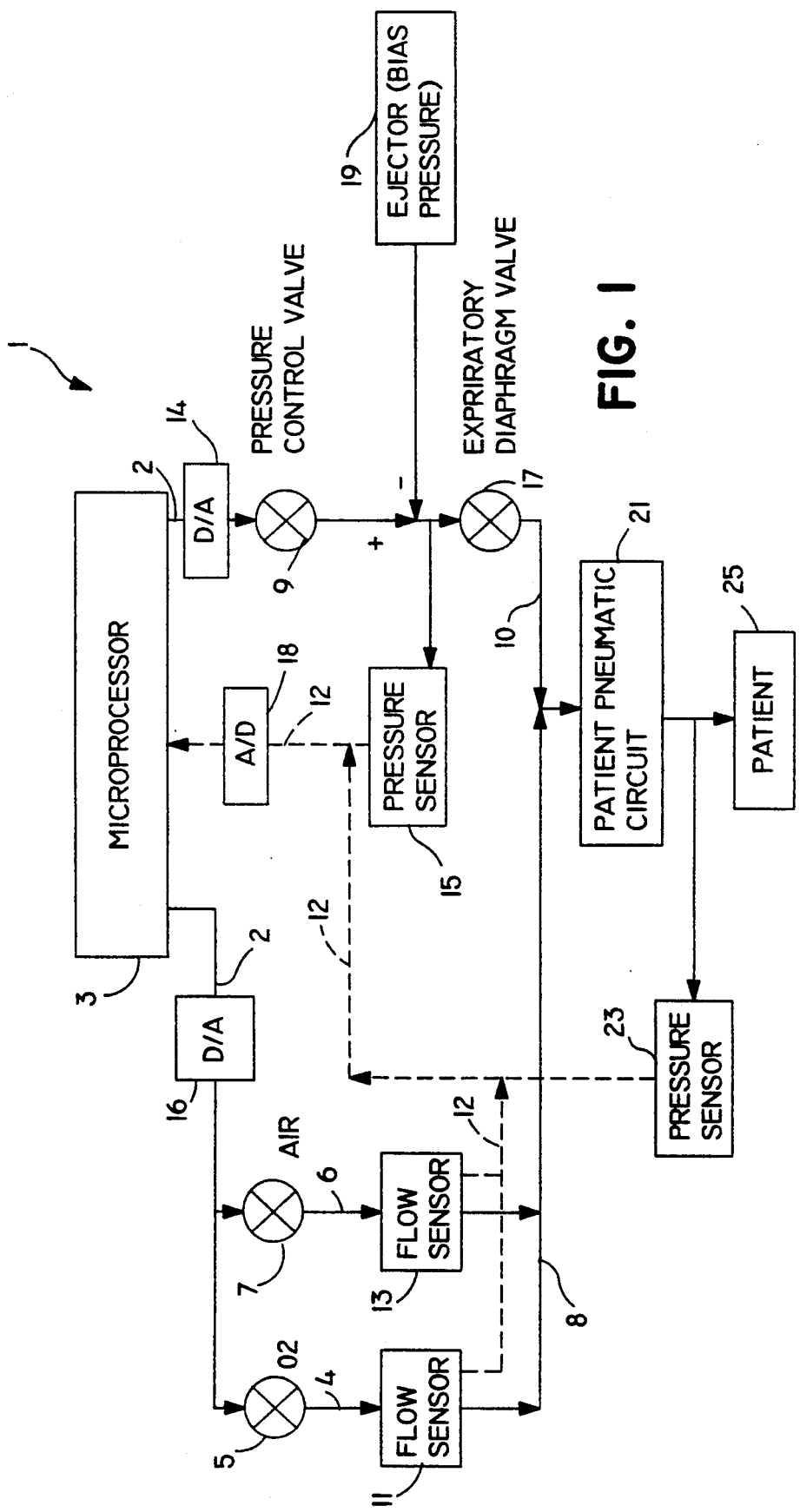
FIG. 1 is a functional block diagram of a medical ventilator in accordance with the present invention.

A functional block diagram of a medical ventilator 1 in accordance with the present invention is shown in FIG. 1. Medical ventilator 1 is controlled by microprocessor 3 which transmits control signals over output signal lines 2 to flow control valves 5 and 7 and pressure control valve 9. Flow control valves 5 and 7 preferably are high speed, flow-regulating solenoid valves which regulate the flow of gas from regulated gas supplies (not shown). Pressure control valve 9 preferably is a high speed, pressure-regulating solenoid valve which applies back pressure to expiratory diaphragm valve 17. Digital output signals from microprocessor 3 are converted to analog signals using a digital to analog convertors 14 and 16 (D/A convertors) before transmission to flow control valves 5 and 7 and pressure control valve 9. The D/A convertor preferably performs this conversion using pulse width modulation (PWM). The analog signals operate the valves through analog current driver amplifiers (also not shown).

Flow control valves 5 and 7 control the flow of gas from sources of oxygen ($O_2$) and air, respectively. A flow of $O_2$ passes from valve 5, through conduit 4, flow sensor 11 and into inspiratory conduit 8. A flow of air passes from valve 7, through conduit 6, flow sensor 13 and into inspiratory conduit 8. Flow sensors 11 and 13 measure the magnitude of flow of gases within conduits 4 and 6, respectively, and transmit signals indicative of these magnitudes back to microprocessor 3 over feedback signal lines 12. Since the output signals from flow sensors 11 and 13, and also the output signals from pressure sensors 15 and 23, are in analog form, all of these feedback signals are passed through analog to digital convertor 18 (A/D convertor), before transmission to microprocessor 3. In a preferred embodiment, a single, multiplexed A/D convertor is used for converting all of these feedback signals to digital format.

A mixed flow of $O_2$ and air passes through inspiratory conduit 8 into the patient pneumatic circuit 21. This circuit comprises the various pneumatic conduits (e.g., the patient's wye piece, mouth piece, etc.) transmitting gas into the mouth of patient 25. The inspiratory pneumatic circuit is a demand-flow system, i.e., all of the gas flowing through flow control valves 5 and 7 and inspiratory conduit 8 enters patient pneumatic circuit 21 and the mouth of patient 25.

The pressure of gas within the mouth of patient 25 is measured by pressure sensor 23. This sensor, which preferably is a piezoresistive pressure sensor, is located on the patient's wye piece and transmits a signal indicative of the actual pressure of gas within the mouth of patient 25 and/or his or her respiratory tract. This sensor also may be located within the mouth or respiratory tract (e.g., the trachea or lungs) of patient 25. The signal from sensor 23 is transmitted through an A/D convertor to microprocessor 3 on feedback signal line 12. This signal first may be transmitted through a digital or analog anti-aliasing filter 49 (shown in FIG. 3) to remove noise above the Nyquist frequency before processing by the A/D convertor.

Expiratory gas from patient 25 passes through patient pneumatic circuit 21, expiratory conduit 10 and into expiratory diaphragm valve 17. Pressure control valve 9 transmits gas from a regulated source (not shown) to the back of expiratory diaphragm valve 17 and controls the pressure applied to the back of the diaphragm of this valve. Pressure sensor 15 measures the actual back pressure on expiratory diaphragm valve 17 and transmits a signal indicative of this pressure through the A/D convertor to microprocessor 3 on feedback signal line 12. Ejector valve 19, which preferably is a venturi valve, establishes a reference back pressure for expiratory diaphragm valve 17 below that of the surrounding atmosphere. Ejector valve 19, therefore, enables the application of a negative back pressure to the diaphragm valve.

Figure 2:
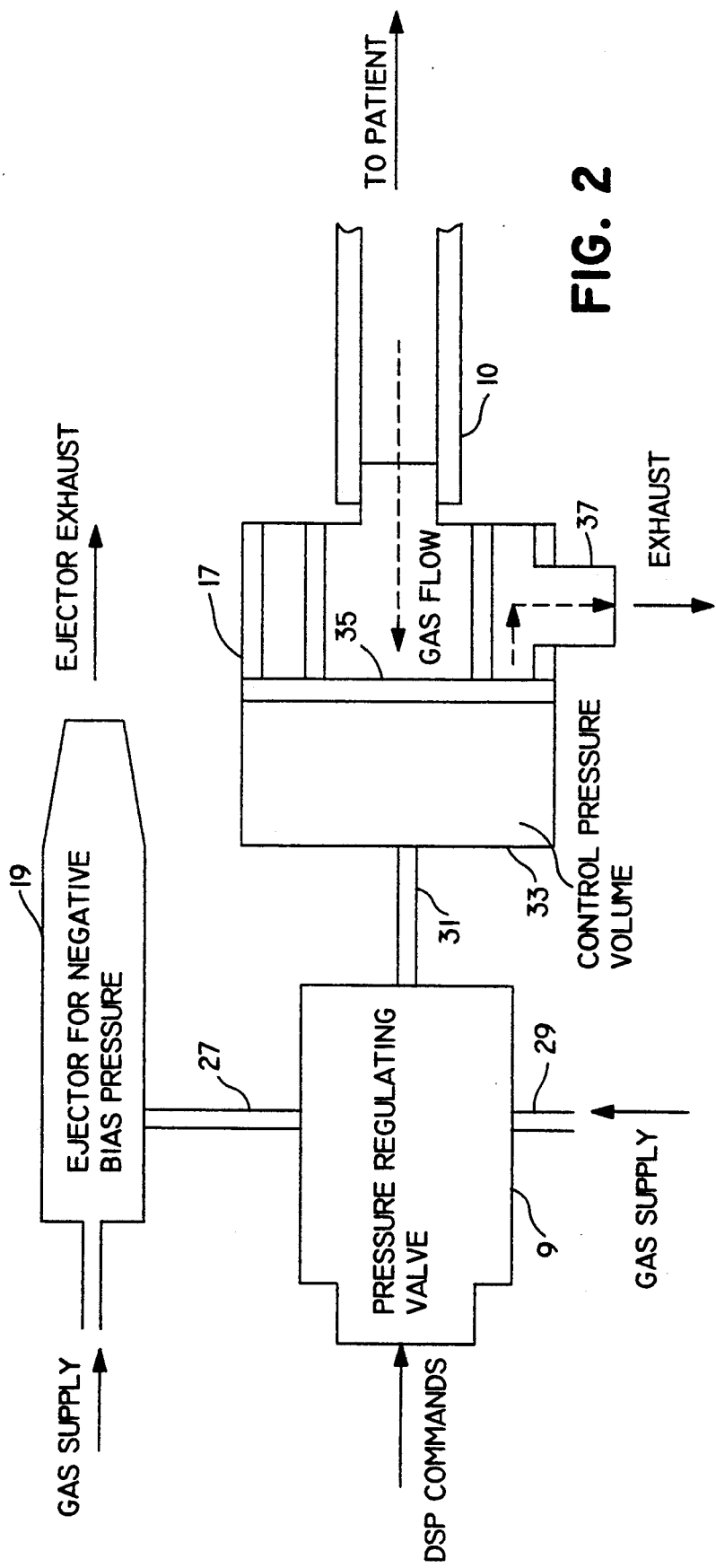
FIG. 2 is a schematic diagram of pressure-control, expiratory-diaphragm and ejector valves in accordance with the present invention

The structure and operation of pressure control valve 9, expiratory diaphragm valve 17 and ejector valve 19 are shown in FIG. 2. Expiratory gas from patient 25 passes through expiratory conduit 10 and impinges upon diaphragm 35. If the pressure within the back chamber 33 of diaphragm valve 17 exceeds the pressure of expiratory gas within expiratory conduit 10 (normally the case during the inspiratory phase of respiration), the diaphragm remains sealed and no gas passes through this valve. On the other hand, if the pressure within back chamber 33 is below that within expiratory conduit 10 (normally the case during the expiratory phase of respiration), diaphragm 35 opens allowing gas to pass through exhaust conduit 37 into the surrounding atmosphere.

The pressure of gas within back chamber 33 is controlled by pressure regulating valve 19 in response to control-signals from microprocessor 3. Pressure regulating valve 9 controls the flow of gas from a regulated supply (not shown) through conduits 29 and 31 into back chamber 33. Ejector valve 19 creates a negative reference pressure within conduit 27 for pressure regulating valve 9. This negative pressure is created by transmitting a flow of gas from a supply (not shown) through ejector 19 which acts as a venturi. In the alternative, a spring or permanent magnet could be used to bias diaphragm 35 against the pressure within back chamber 33. The use of a venturi is preferred, however, because the magnitude of negative pressure can be controlled and the dynamics of feedback control are simplified.

The provision of a negative reference pressure for pressure regulating valve 9 lowers the non-linear, saturation threshold of this valve, enabling a higher speed of response, and reduces expiratory resistance, particularly at pressures close to that of the surrounding atmosphere. The existence of a negative reference pressure also results in the opening of diaphragm valve 17 in the event of failure by pressure regulating valve 9, insuring an unobstructed airway between the patient's mouth and the atmosphere.

In an alternative embodiment, expiratory conduit 10 includes a second venturi or other negative pressure means (not shown), in pneumatic communication with exhaust conduit 37, for creating an exhaust pressure below that of the surrounding atmosphere. This second means for negative pressure also lowers the non-linear, saturation threshold of the pressure-regulating valve and, because of the ability of medical ventilator 1 to precisely control mouth pressure, poses no risk to patient-safety.

Figure 3:
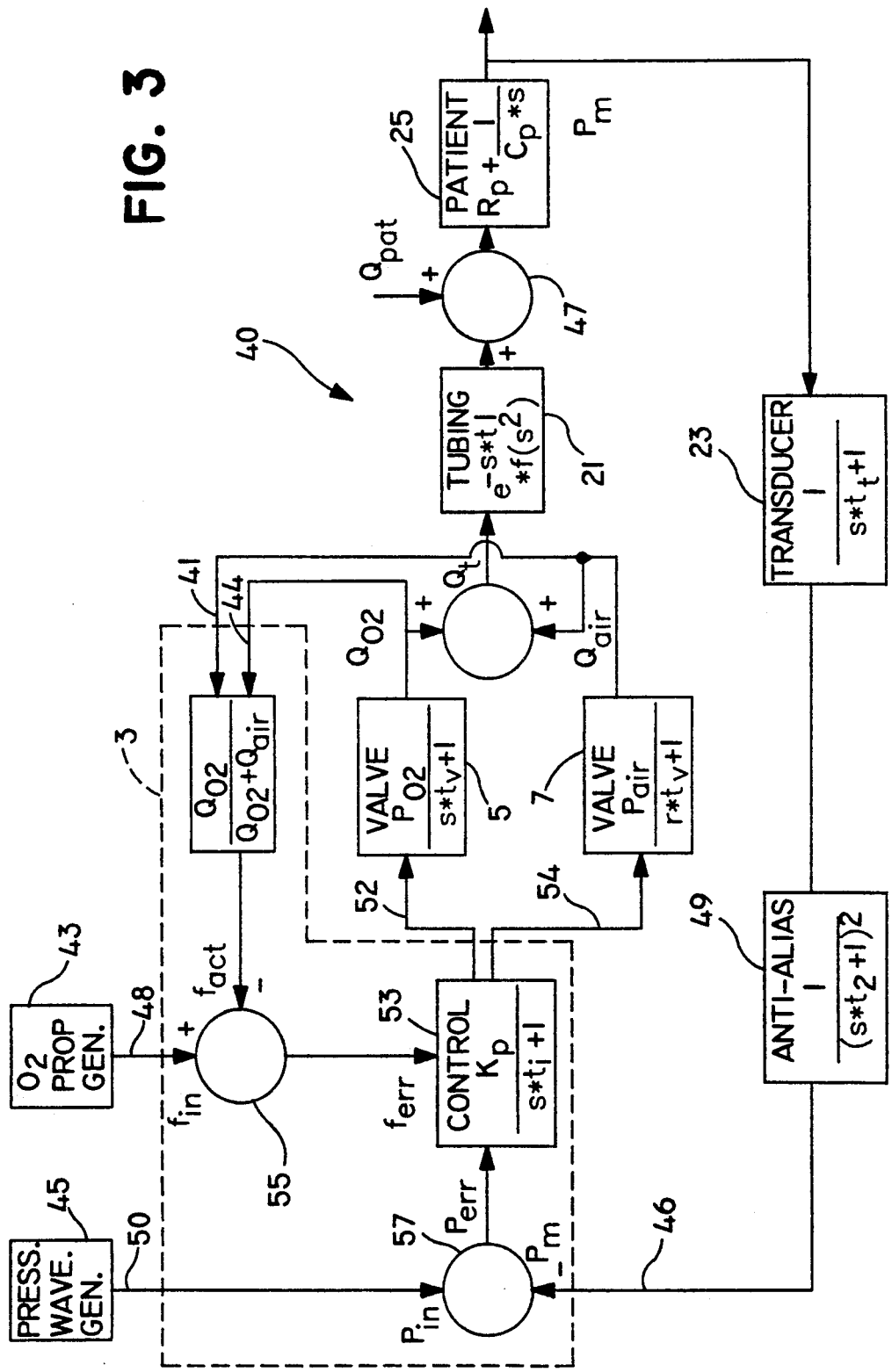
FIG. 3 is a schematic diagram of the inspiratory pneumatic circuit and control loop of the present invention.

A schematic diagram of the inspiratory pneumatic circuit and control loop 40 of medical ventilator 1 is shown in FIG. 3. The functions performed by microprocessor 3 are shown enclosed within the broken line of this figure.

Microprocessor 3 receives input signals from pressure waveform signal generator 45 and $O_2$ proportional signal generator 43 over lines 50 and 48, respectively. Pressure waveform signal generator 45 can generate any selected pressure waveform signal ($P_{in}$) as a function of time. The form of this signal is controlled by the ventilator's operator (generally a physician) in accordance with the ventilatory mode selected to assist the patient. The particular waveform generated by pressure waveform signal generator 45 can be in response to a signal from a separate monitoring or selecting system (not shown) which may monitor the patient's respiratory response and make this selection based on such monitoring. Because of the ability of medical ventilator 1 to precisely control a patient's mouth-pressure, the mode of ventilation need not be restricted to present ventilatory techniques. In fact, it is expected that medical ventilator 1 will assist physicians to develop completely new ventilatory techniques.

$O_2$ proportional signal generator 43 provides an input signal ($f_{in}$) to microprocessor 3 indicative of the desired proportion of oxygen in the total flow of oxygen and air provided to patient 25. This signal either may be constant or also may vary in accordance with any selected function of time.

As discussed above, feedback input signals are provided to microprocessor 3 on lines 41 and 44 from flow control valves 7 and 5, respectively, via flow control sensors 13 and 11 (shown in FIG. 1). These signals are indicative of the magnitude of the instantaneous, actual flow of gas passing through these valves. A feedback signal also is provided to microprocessor 3 on line 46 from pressure sensor 23, generally located in the patient's wye piece, via anti-alias filter 49. This signal is indicative of the instantaneous, actual pressure of gas within, or substantially within, the patient's mouth or respiratory tract. Anti-alias filter 49 may be omitted if the signal from pressure sensor 23 is substantially attenuated.

Microprocessor 3 provides flow-control command signals to valves 5 and 7 on lines 52 and 54, respectively, for controlling the flow of $O_2$ and air into inspiratory conduit 8. The total flow of gas within the inspiratory conduit ($Q_t$) flows through patient pneumatic circuit 21 and into the mouth of patient 25. The effect, if any, upon this flow induced by the patient's respiratory function is represented by flow summing block 47.

Microprocessor 3 repeatedly calculates at block 51 the proportion of oxygen flowing from valve 5 to the total flow of oxygen and air flowing from both valves 5 and 7. A signal indicative of this actual proportion ($f_{act}$) is transmitted to flow error block 55. The difference between fact and $f_{in}$ (the desired O₂ proportion) is calculated at block 55, and a signal indicative of this difference ($f_{err}$) is transmitted to the inspiratory-control function executed by the microprocessor at block 53. The magnitudes of the signals transmitted from microprocessor 3 on lines 52 and 54 to valves 5 and 7, respectively, continuously adjust these valves to compensate for differences between the desired proportion of O₂ in $Q_t$ (the total flow of O₂ and air) and the actual proportion.

Microprocessor 3 also repeatedly determines at block 57 the difference between the patient's actual mouth pressure ($P_m$), represented by the signal on line 46, and the pressure from the pressure waveform signal generator, represented by the signal on line 50 ($P_{in}$). A signal representing this difference ($P_{err}$) is transmitted to the inspiratory-control function executed by the microprocessor at block 53.

An understanding of the dynamics of inspiratory pneumatic circuit and control loop 40 requires analysis in the frequency domain. The Laplace transfer functions for flow control valves 5 and 7, patient pneumatic circuit 21, patient 25, pressure sensor 23 and anti-alias filter 49, derived for each of these elements, are shown within the corresponding blocks representing these elements in FIG. 3. In all of these functions, s represents the Laplace operator.

The linearized Laplace transfer function for flow control valve 5 is:

$$\frac{P_{o2}}{s*t_v + 1} \quad [1]$$

wherein, $P_{o2}$=the pressure of the regulated supply of O₂, and $t_v$=the time constant of flow-control valve 5.

The Laplace transfer function for flow control valve 7 is:

$$\frac{P_{air}}{s*t_v + 1} \quad [2]$$

wherein, $P_{air}$=the pressure of the regulated supply of air, and $t_v$=the time constant of flow control valve 7. The form of the Laplace transfer function of patient pneumatic circuit 21, which behaves as a second order system with a time delay, is:

$$e^{-s*t_1}*f(s^2) \quad [3]$$

wherein, $t_1$=the time constant of the patient pneumatic circuit.

The Laplace transfer function of the patient's effect upon the inspiratory control loop is:

$$R_p + \frac{1}{C_p*s} \quad [4]$$

wherein, $R_p$ is the resistance of the patient's respiratory tract and $C_p$ is the compliance of the patient's respiratory tract.

The Laplace transfer function for pressure sensor 23 is:

$$\frac{1}{s*t_t + 1} \quad [5]$$

wherein, $t_t$=the time constant of this transducer.

The Laplace transfer function for anti-alias filter 49 is:

$$\frac{1}{(s*t_2 + 1)^2} \quad [6]$$

wherein, $t_2$=the time constant of this filter.

The Laplace transform of the inspiratory control function has the following form:

$$\frac{K_p}{s*t_1 + 1} \quad [7]$$

wherein, $K_p$=a proportional gain constant, and $t_1$=the inspiratory-control function time constant. This time constant is equivalent to $R_p*C_p$.

The error-compensation provided by the inspiratory-control function results in a pole-zero cancellation when combined with the patient's effect upon the inspiratory control loop, equation [4], as shown in the following equation:

$$\frac{K_p}{t_1*s + 1} * \frac{R_p*C_p*s + 1}{C_p*s} = \frac{K_p}{C_p*s} \quad [8]$$

Since the value of $R_p$ varies as a function of the flow of gas into the patient's respiratory tract, and the values of $R_p$ and $C_p$ vary from patient to patient, the use of a simple, linear compensation algorithm (a constant $t_1$ based upon nominal values for $R_p$ and $C_p$) results in degradation of the controller's response as the actual values of $R_p$ and $C_p$ move away from these nominal values. In order to accurately control mouth-pressure, therefore, an adaptive feedback control system is preferred. The system must adapt such that $t_1*s+1$, the lag term of the inspiratory control function and the lead term of the patient's effect upon the system, cancel for any patient and throughout the patient's respiratory cycle.

The value of $P_m$ at any point in time (T) measured from the beginning of inspiration is represented by the following equation:

$$P_m = R_p*Q + \frac{\int_o^T Q\, dt}{C_p} \quad [9]$$

wherein, Q=the instantaneous flow of gas into the patient's respiratory tract, and T=the time of inspiration from the beginning of a breath. Although the precise manner of variation of $R_p$ with Q is complex, a good approximation of this variation is achieved by assuming that $R_p$ varies linearly with Q. Thus, at the instant of initiation of a breath, the value of $P_m$ can be represented by the following equation:

$$P_m = R_p'*Q^2 \quad [10]$$

wherein, $R_p'$ equals the "second order resistance" of the patient's respiratory tract, conforming to the following equation:

$$R_p'^* Q^2 = R_p^* Q \qquad [11]$$

$R_p'$ is called a second order resistance because it is expressed in units of pressure divided by the rate of flow squared. The actual resistance $R_p$, therefore, is called the first order resistance because it is expressed in units of pressure divided by the rate of flow.

Since $t_1 = R_p^* C_p$, then $t_1 = R_p'^* C_p^* Q = K^* Q$, where $K = R_p'^* C_p$. In order to determine $t_1$, therefore, the value of K must be determined for each patient and this value then varied linearly with the magnitude of Q. Satisfactory results are achieved, however, if a nominal value of $C_p$ is used for all patients (e.g., 50 ml/cm $H_2O$), and patient to patient and Q variations are made for $R_p$ only. This phenomenon apparently results from the appearance of $C_p$ in both the numerator and denominator of equation [8], largely cancelling variations in response due to variations in $C_p$. Patient to patient variations in $R_p$, viz., the value of $R_p'$, are approximated by measuring $Q^2$ (or the magnitude of the control function's output signal controlling $Q^2$) and $P_m$ at the instant of initiation of each inspiration. $P_m$ then is divided by $Q^2$ to determine $R_p'$.

In order to create a low pass, digital filter which executes the inspiratory control function such that the lag term in this function continuously cancels the lead term in the patient's function, the value $t_1^* s + 1$ is transformed to the Z domain using the backwards difference technique. In accordance with this technique:

$$s = \frac{1 - Z^{-1}}{T} \qquad [12]$$

wherein T = the time between updating of the digital coefficients, e.g., 0.001 secs.

Therefore, if $\tau$ = the value of $t_1$, $\tau_1$ = the value of $t_1$ t time 1 and $\tau_0$ = the value of $t_1$ at time 0, then $$\tau^* s + 1 = \frac{\tau^*[1 - Z^{-1}]}{T} + 1 = \left[\frac{\tau_1}{T} + 1\right] - \frac{\tau_0}{T} \cdot Z^{-1} \qquad [13]$$

Since $\tau^* s + 1$ is inverted in the inspiratory control transfer function, the form of this function in the Z-domain is:

$$\frac{K_p}{\tau^* s + 1} = \frac{K_p}{\left[\frac{\tau_1}{T} + 1\right] - \frac{\tau_0}{T} \cdot Z^{-1}} \qquad [14]$$

If the Z-domain transfer function is represented in terms of the inspiratory digital coefficients $A_1$, $C_i$, and $G_i$ (equivalent to $K_p$), this function has the following form:

$$\frac{A_i^* G_i}{1 + C_i^* Z^{-1}} \qquad [15]$$

Therefore, $$A_i = \frac{1}{\frac{\tau_1}{T} + 1} \qquad [16]$$

and, $$C_i = \frac{-\frac{\tau_0}{T}}{\frac{\tau_1}{T} + 1} \qquad [17]$$

where $\tau_0 = K \cdot Q \cdot Z^{-2} \qquad [17a]$ $\tau_1 = K \cdot Q \cdot Z^{-1} \qquad [18]$ In the above formula, Q is the absolute value of the flow of gas within the inspiratory conduit, and K is a constant equivalent to $R_p' C_p$ which varies from patient to patient.

From system simulations, the following values for $G_i$ and for initialization of $A_i$ and $C_i$ were derived:

$G_i = 2$
$A_i = 0.008$
$C_i = 0.992$

Figure 4:
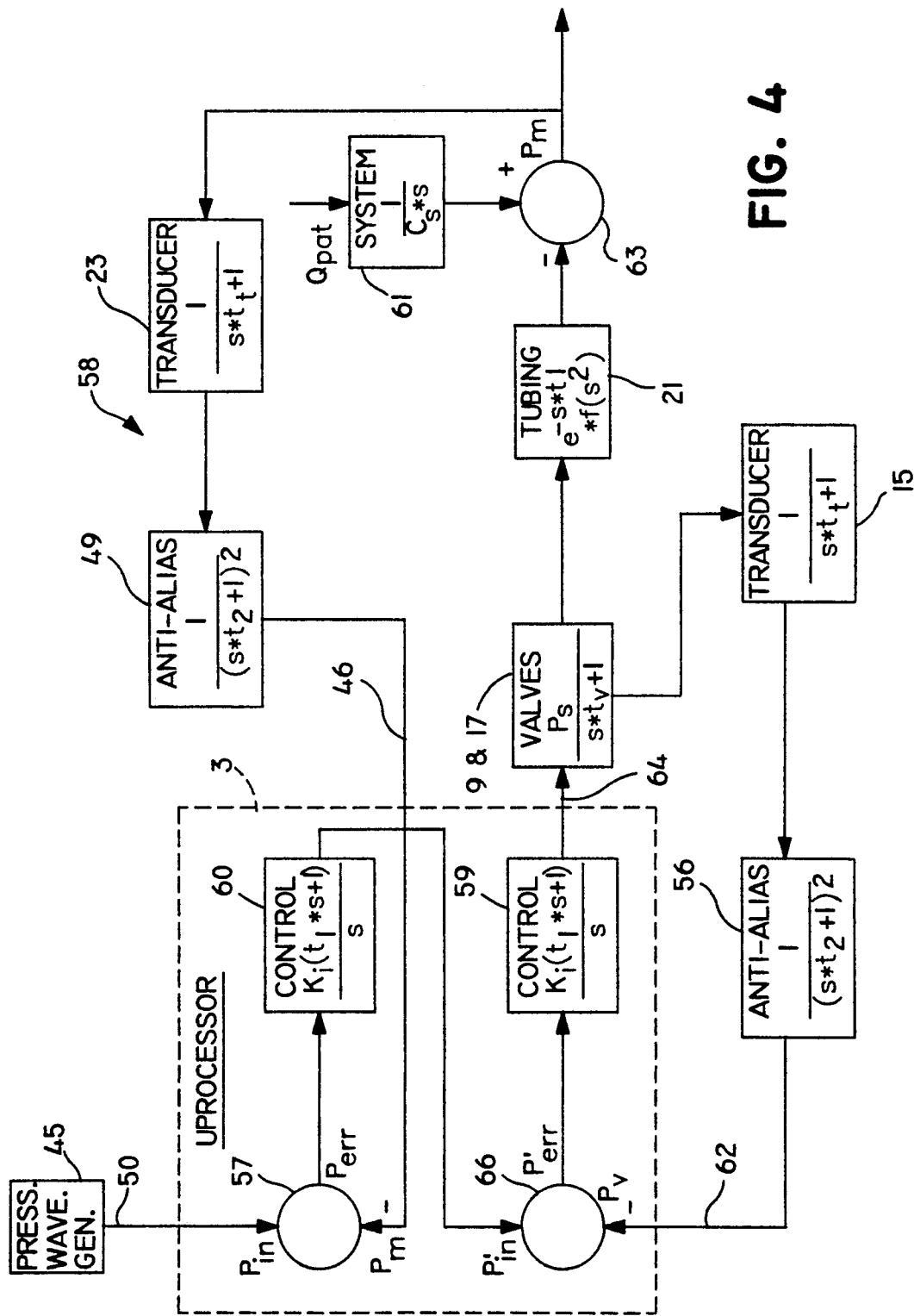
FIG. 4 is a schematic diagram of the expiratory pneumatic circuit and control loop of the present invention.

A schematic diagram of expiratory pneumatic circuit and control loop 58 of medical ventilator 1 is shown in FIG. 4. As in FIG. 3, the functions performed by microprocessor 3 are shown enclosed within the broken line of FIG. 4, and the linearized Laplace transfer functions, derived for the elements of this circuit, are shown within the blocks representing these elements. Since the effects upon expiratory control resulting from variations in the resistance and compliance of the patient's respiratory tract are less significant in the expiratory circuit, an adaptive controller is not preferred for expiratory control.

An expiratory output command signal from microprocessor 3 is transmitted to pressure control valve 9 on line 64. This valve provides a back pressure to expiratory diaphragm valve 17 corresponding to the magnitude of this signal. This back pressure is effectively transmitted through the patient pneumatic circuit 21 to the mouth of patient 25. The effects on expiratory flow initiated by patient 25 are integrated by the compliances of the patient pneumatic circuit, at block 61, causing a pressure disturbance at summing point 63.

The actual pressure of gas within, or substantially within, the patient's mouth or respiratory tract is transmitted to microprocessor 3 using the same circuit as that used for inspiratory pneumatic and control loop circuit 40. This actual pressure is measured by pressure sensor 23 whose output is provided to microprocessor 3 via anti-alias filter 49 and an A/D convertor (not shown). The microprocessor generates a pressure error signal ($P_{err}$) at pressure error block 57 in a manner identical to that for inspiratory control. This error signal is provided to a first expiratory-control function at block 60, which responds with a corresponding compensation signal.

In order to more precisely control the back pressure applied to diaphragm valve 17, expiratory pneumatic circuit and control loop 58 uses a second closed loop controller for controlling this pressure. Rather than apply the compensation output signal from the first expiratory-control function directly to pressure-control valve 9 (which does not account for the pressure, if any, currently applied by this valve), therefore, this signal is an input pressure signal $P'_{in}$ to pressure-error block 66 for this second closed loop. Pressure sensor 15, which measures the actual back pressure on the diaphragm valve, provides on line 62, via anti-alias filter 56 and an A/D convertor, the feedback pressure ($P_v$) for pressure-error block 66. The algorithm executed by the microprocessor at this block generates a pressure-error signal ($P'_{err}$) which is transmitted to a second expiratory-control function (also executed by microprocessor 3) at block 59. The output from this second expiratory-control function is transmitted on line 64 to pressure-control valve 9 which controls the back pressure on expiratory diaphragm valve 17 such that $P_v$ tracks the output from the second expiratory control function ($P'_{in}$), and, concomitantly, $P_m$ tracks $P_{in}$ during periods requiring expiratory flow.

The linearized Laplace transfer functions for patient pneumatic circuit 21, pressure sensors 15 and 23, and anti-alias filters 49 and 56 have the same form as for the inspiratory circuit, equations [3], [5] and [6], respectively.

The Laplace transfer function for the combined effect of valves 9 and 17 is:

$$\frac{P_s}{s^*t_v + 1} \quad [19]$$

wherein, $P_s$ = the pressure of gas transmitted from pressure control valve 9 and $t_v$ = the time constant of these valves.

The Laplace transfer function for the first and second expiratory control functions have the following form:

$$\frac{K_i^*[t_1^*s + 1]}{s} \quad [20]$$

wherein, $K_i$ = the integral gain constant, and $t_1$ = the expiratory control function time constant. In this case, $t_1$ is a constant value equal to:

$$\frac{K_p}{K_i} \quad [21]$$

wherein, $K_p$ equals the proportional gain constant.

In order to create a low pass, digital filter which executes the first and second expiratory control functions, these functions are transformed to the Z-domain using the bi-linear transform technique. In accordance with this technique:

$$s = \frac{2^*(1 - Z^{-1})}{T^*(1 + Z^{-1})} \quad [22]$$

wherein, T = the time between updating of the digital coefficients, e.g., 0.001 secs.

Therefore, $$\frac{K_i^* \left( \frac{K_p}{K_i} {}^*s + 1 \right)}{s} = \frac{\frac{2^*K_p^*(1 - Z^{-1})}{T^*(1 + Z^{-1})} + K_i}{\frac{2^*(1 - Z^{-1})}{T^*(1 + Z^{-1})}} = \quad [23]$$

$$\frac{2^*K_p^*(1 - Z^{-1}) + K_i^*T^*(1 + Z^{-1})}{2^*(1 - Z^{-1})} =$$

$$\frac{(2^*K_p + K_i^*T) + Z^{-1*}(K_i^*T - 2^*K_p)}{2 - 2^*Z^{-1}}$$

If the Z-domain transfer function for the first expiratory control function is represented in terms of the expiratory digital coefficients, $A_e$, $B_e$ and $C_e$, this function has the following form:

$$\frac{A_e + B_e^*Z^{-1}}{1 + C_e^*Z^{-1}} \quad [24]$$

wherein, $$A_e = K_p + \frac{K_i^*T}{2} \quad [25]$$

$$B_e = \frac{K_i^*T}{2} - K_p \quad [26]$$

$$C = -1 \quad [27]$$

Since the second expiratory control function has the same form, the expiratory digital coefficients for this function, $D_e$, $E_e$ and $F_e$, also have the form of equations [25], [26] and [27], respectively.

Figure 5:
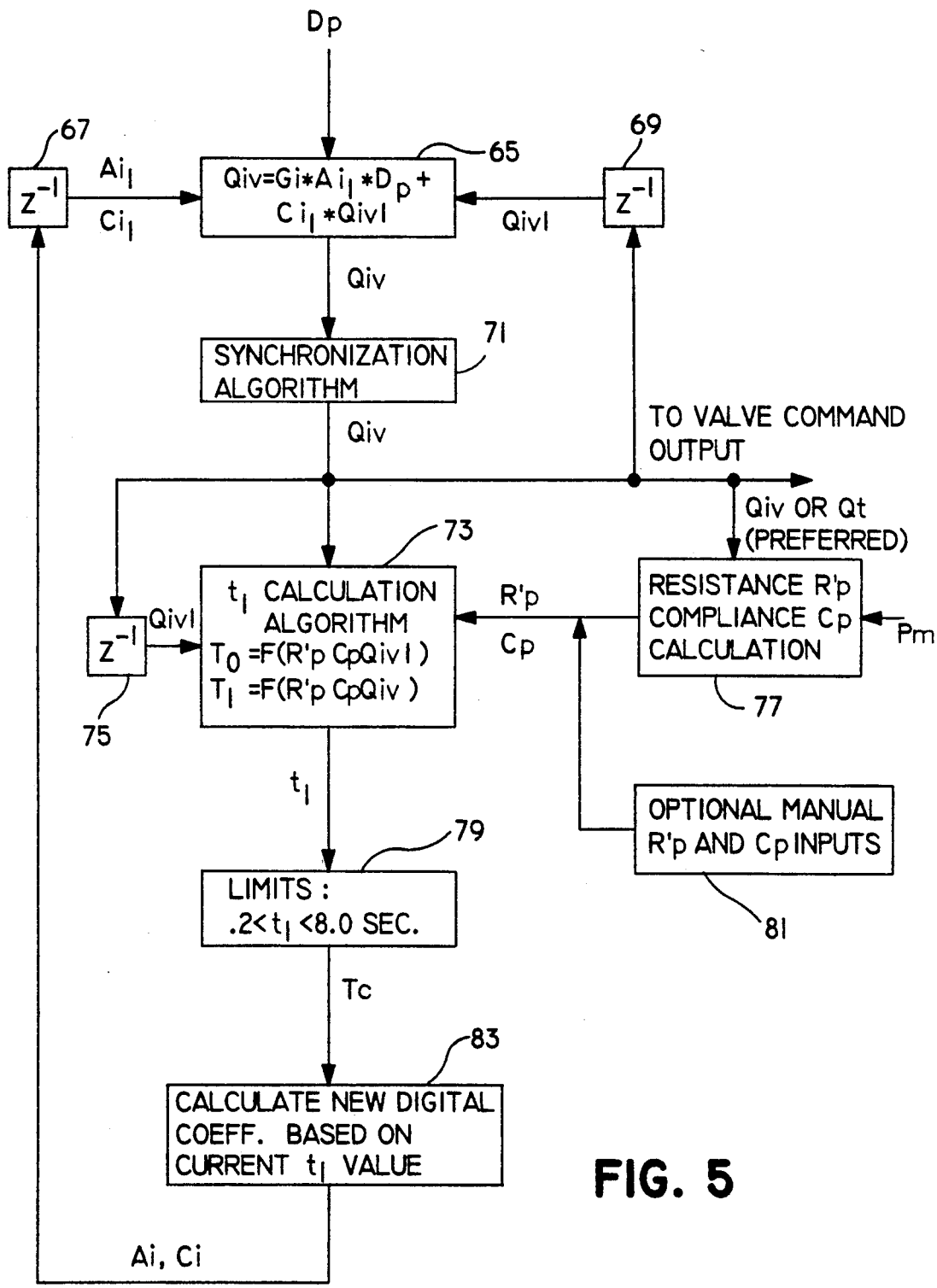
FIG. 5 is a flow diagram illustrating the steps of inspiratory control in accordance with the present invention.

From system simulations, the following values were derived for these expiratory coefficients:
$A_e = 0.923$;
$B_e = -0.877$;
$C_e = 1$;
$D_e = 1.212$;
$E_e = -1.188$; and
$F_e = 1$ FIG. 5 is a flow diagram showing the steps of the inspiratory control function, as executed by microprocessor 3. The digital pressure-error signal $D_p$ (equivalent to $P_{err}$), generated by the microprocessor at pressure-error block 57 (FIG. 3), is transmitted to the inspiratory control function algorithm at block 65. This algorithm also receives as inputs the last (delayed by one clock cycle) flow-command output from the inspiratory control function ($Q_{iv1}$) and the last (delayed by one clock cycle) values of the inspiratory digital coefficients ($A_{i1}$ and $C_{i1}$) used to generate this output, via blocks 69 and 67, respectively. The flow command output ($Q_{iv}$) is generated at block 65 in accordance with the following equation:

$$Q_{iv} = G_i^*A_{i1}^*D_p + C_{i1}^*Q_{iv1} \quad [28]$$

The flow command output $Q_{iv}$ is transmitted to the synchronization algorithm 71, explained below in connection with FIG. 7, and the $Q_{iv}$ output from the synchronization algorithm (which may be modified by this algorithm) is transmitted to the time-constant calculation algorithm at block 73.

The time-constant calculation algorithm also receives as inputs $R_p$ (second order resistance) and $C_p$ block 77, and $Q_{iv1}$ from block 75. The time-constant calculation algorithm calculates $\tau_0$ and $\tau_1$ in accordance with formulas [17a] and [18] (using $Q_{iv}$ and $Q_{iv1}$ as representative of ($Q^*Z^{-1}$) and ($Q^*Z^{-2}$), respectively) and provides these outputs to the time-constant limits algorithm at block 79. This algorithm sets limits of between 0.2 secs. and 8.0 secs. for $t_1$ ($\tau_0$ and $\tau_1$) to prevent a runaway condition.

The resistance/compliance algorithm at block 77 receives as inputs $Q_{iv}$ and $P_m$ and calculates the second order resistance in accordance with equation [10] (Pm divided by $Q^2_{iv}$). In the alternative, rather than using $Q_{iv}$ for this calculation, the measured value of inspiratory flow ($Q_I$) can be used. While the use of $Q_I$ is preferred for greater accuracy, the use of $Q_{iv}$ requires no addition to the system (the value of $Q_{iv}$ already is available). The resistance/compliance algorithm also can calculate the value of $C_p$, based on system-monitoring of pressure and flow, or a nominal value for $C_p$ may be used (e.g., 50 ml/cm $H_2O$). A capability also exists for manually entering values for $R_p'$ and $C_p$ into the time-constant calculation algorithm, as indicated at block 81.

Finally, at block 83, the updated values of the inspiratory digital coefficients, $A_i$ and $C_i$, are calculated in accordance with equations [16] and [17] based upon the updated values of $\tau_0$ and $\tau_1$.

Figure 6:
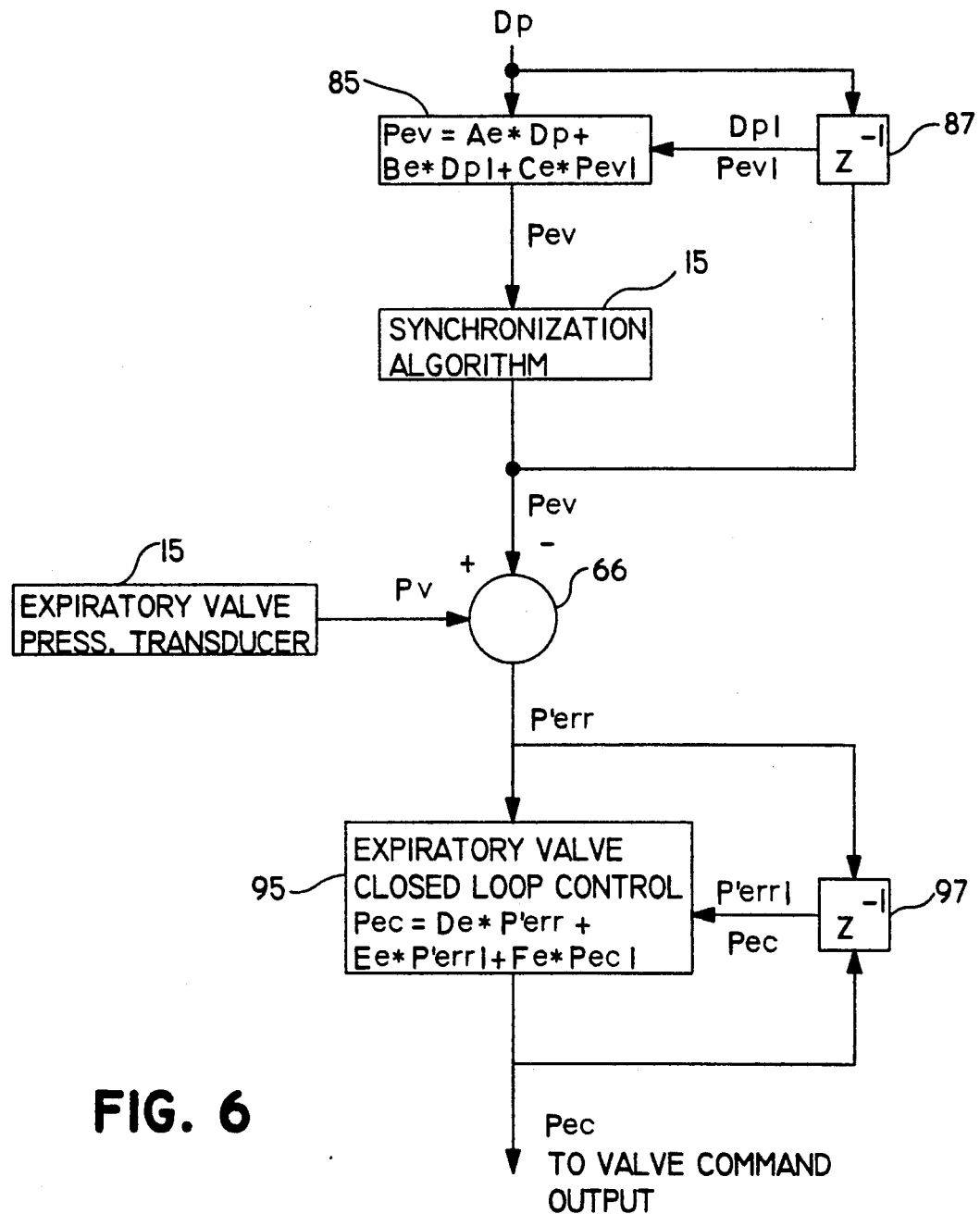
FIG. 6 is a flow diagram illustrating the steps of expiratory control in accordance with the present invention.

FIG. 6 is a flow diagram showing the steps of the first and second expiratory control functions, as executed by microprocessor 3. The digital pressure-error signal $(D_p)$ from pressure-error block 57 is transmitted to the first expiratory-control function at block 85. The first expiratory-control function also receives as inputs, from block 87, the last (delayed by one clock cycle) pressure-error signal $(D_{p1})$ and the last (delayed by one clock cycle) pressure-command output from the first expiratory control function $(P_{ev1})$ The pressure-command output $P_{ev1}$ is provided to the first expiratory-control function after modification, if any, by the synchronization algorithm at block 89, discussed below in connection with FIG. 7.

The output $(P_{ev})$ of the first expiratory-control function is generated at block 85, using the expiratory digital coefficients $A_e$, $B_e$ and $C_e$, in accordance with the following equation:

$$P_{ev} = A_e \cdot D_p + B_e \cdot D_{p1} + C_e \cdot P_{ev1} \qquad [29]$$

The output $P_{ev}$ is transmitted to the synchronization algorithm at block 89. The $P_{ev}$ output from the synchronization algorithm is transmitted to pressure-error block 66 which compares this pressure-command signal with the actual back pressure applied to expiratory diaphragm valve 17 $(P_v)$ by pressure control valve 9, as measured by pressure sensor 15. The output signal from pressure-error block 66 $(P'_{err})$ represents the difference between the actual back pressure existing on expiratory diaphragm valve 17 and the back pressure commanded by the first expiratory-control function.

The signal $P'_{err}$ is provided to the second expiratory-control function at block 95, which also receives as inputs $P'_{err1}$ and $P_{ec1}$, the last (delayed by one clock cycle) output from pressure-error block 66 and the last (delayed by one clock cycle) output from the second expiratory-control function, respectively. The output $P_{ec}$ of the second expiratory-control function is generated using the expiratory digital coefficients, $D_e$, $E_e$ and $F_e$, in accordance with the following equation:

$$P_{ec} = D_e \cdot P_{err} + E_e \cdot P_{err1} + F_e \cdot P_{ec1} \qquad [30]$$

The output $P_{ec}$ is transmitted to pressure-control valve 9, and the magnitude of back pressure applied by this valve equals the magnitude of this signal. This back pressure controls $P_m$ such that $P_m$ tracks the input pressure waveform $P_{in}$ during periods requiring expiratory flow.

Microprocessor 3 independently executes the inspiratory and expiratory control algorithms repeatedly as interrupt driven algorithms. During each interrupt period, microprocessor 3 also executes a synchronization algorithm for controlling and coordinating the separate inspiratory and expiratory command signals. The synchronization algorithm controls the inspiratory and expiratory pneumatic circuits and control loops such that the effects of each are exclusive while mouth-pressure is continuously controlled. Since both the inspiratory and expiratory pneumatic circuits are inherently non-linear, i.e., the inspiratory circuit only can transmit gas into the patient's mouth and the expiratory circuit only can transmit gas from the patient's mouth, separate, independent inspiratory and expiratory control functions, both running simultaneously and continuously, are necessary to continuously control mouth-pressure throughout the respiratory cycle. The synchronization algorithm selects for the control of mouth-pressure at any given time the output from the control function which has the capacity to control. There are no fixed or set periods for inspiratory and expiratory control. The selection is made only on the basis of which controller at the particular time has the capacity to effect the desired result. The synchronization algorithm, moreover, provides for the transition between inspiratory and expiratory control smoothly, such that the patient feels as if he or she is breathing under natural circumstances.

Figure 7:
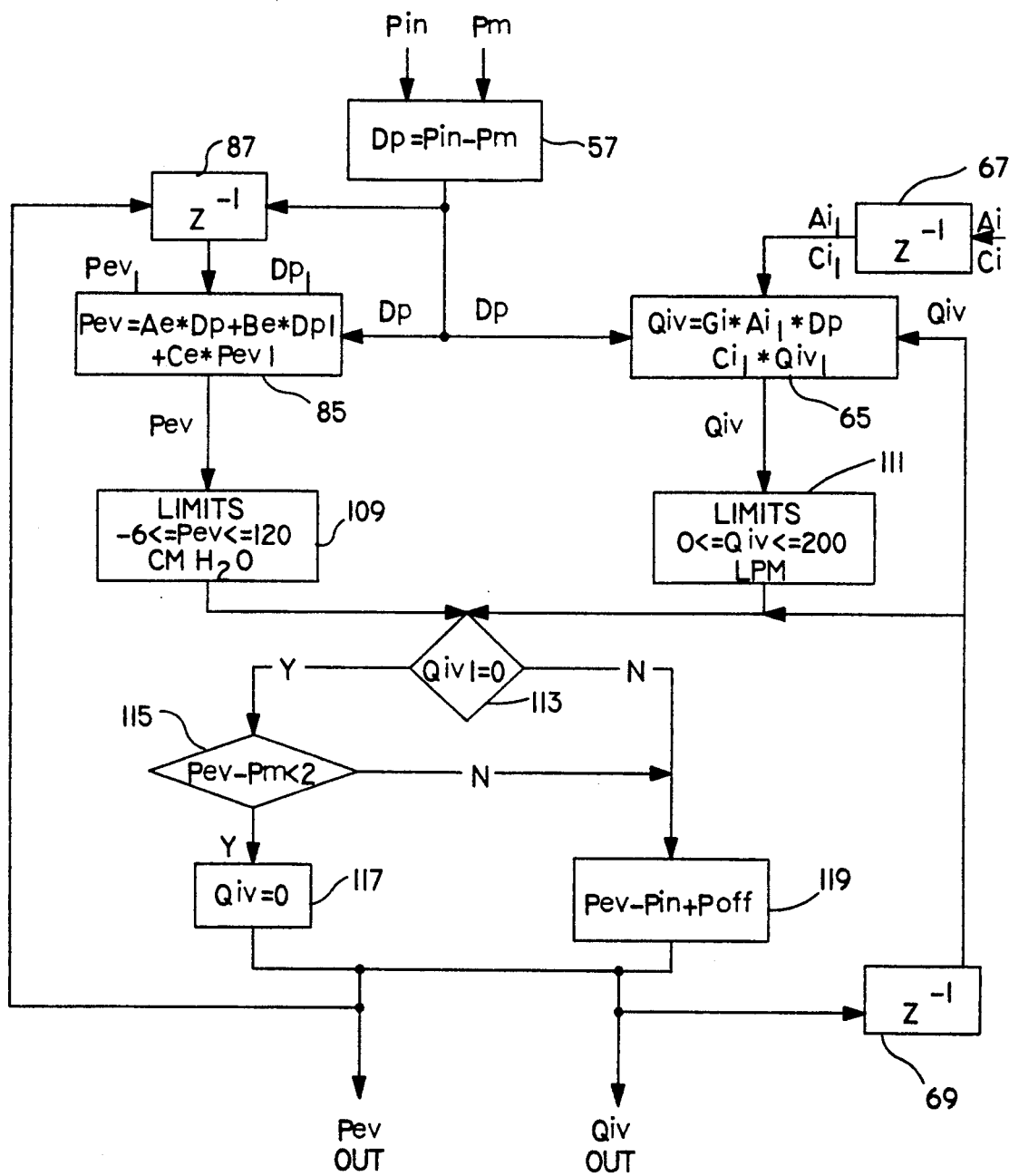
FIG. 7 is a flow diagram illustrating the steps of the synchronization algorithm of the present invention.

FIG. 7 is a flow diagram showing the steps of the synchronization algorithm, as executed by microprocessor 3. The initial steps of this diagram, blocks 57, 65, 67, 85 and 87, resulting in the generation of $P_{ev}$ and $Q_{iv}$, respectfully, are discussed above in connection with FIGS. 5 and 6. The inspiratory output $Q_{iv}$ is transmitted to the inspiratory output limits algorithm at block 111 which sets limits on this output. These limits restrict $Q_{iv}$ to a value greater than, or equal to, zero liters per minute and less than, or equal to, 200 liters per minute. Control of the $Q_{iv}$ output then passes to decisional block 113.

The expiratory output $P_{ev}$ is transmitted to the expiratory output limits algorithm at block 109 where, in a manner similar to the inspiratory output, limits are set on $P_{ev}$. These limits restrict $P_{ev}$ to a value greater than or equal to $-6$ cm $H_2O$ and less than or equal to 120 cm $H_2O$. After the placing of these limits, control of the $P_{ev}$ output, like the $Q_{iv}$ output, passes to decisional block 113.

A determination is made at decisional block 113 whether the last output of the inspiratory control function $(Q_{iv1})$ equals zero. A value for $Q_{iv1}$ of zero (no flow through flow-control valves 5 and 7) means that, during the last clock cycle, either mouth-pressure was under the control of expiratory pneumatic circuit and control loop 58 and control loop 58 retains the capacity to control mouth pressure, or, during that cycle, mouth-pressure was under the control of inspiratory pneumatic circuit and control loop 40 and control loop 40 lost the capacity to control mouth-pressure. If the output from the inspiratory control function is zero, it indicates that the inspiratory control function is attempting to achieve mouth-pressure control by withdrawing gas from the inspiratory branch (an impossibility). Control, therefore, is passed to decisional block 115 which determines whether the value of the expiratory output $P_{ev}$ minus the value of actual mouth-pressure is less than 2 cm $H_2O$. If $P_{ev} - P_m$ is less than 2 cm $H_2O$, it means that the expiratory circuit retains the capacity to control mouth-pressure, i.e., to cause actual mouth-pressure to track the desired pressure $(P_{in})$. In this case, control is passed to block 117 which sets the value of $Q_{iv}$ to zero, leaves the value of $P_{ev}$ at the value received by the synchronization algorithm, and causes the transmission of these values as the $P_{ev}$ and $Q_{iv}$ outputs from the synchronization algorithm.

If at decisional block 115 the value of $P_{ev}-P_m$ is greater than 2 cm $H_2O$, it means that the expiratory circuit has lost the capacity to control mouth-pressure and is raising the back pressure on expiratory diaphragm valve 17 in a vain attempt to maintain control. In this case, control is transferred to block 119 which sets the value of $P_{ev}$ to a pressure equal to a predetermined incremental pressure ($P_{off}$) plus $P_{in}$, leaves the value of $Q_{iv}$ as received by the synchronization algorithm, and cause the transmission of these values as the $P_{ev}$ and $Q_{iv}$ outputs from the synchronization algorithm. Since the value of $P_{off}$ is only several centimeters of $H_2O$, the sealing pressure on diaphragm valve 17 during inspiratory control closely tracks the desired pressure and is always only several centimeters above this pressure. This closely tracking sealing pressure enables a quick transfer to expiratory control if necessary. The provision of a quick, smooth transfer is particularly helpful if the patient attempts to breath out during inspiration (e.g., a sudden cough). The over pressure causes a quick transition to expiratory control which quickly vents the over pressure with little patient discomfort.

Finally, a finding at decisional block 113 that the value of $Q_{iv1}$ is not equal to zero means that, during the last clock cycle, mouth-pressure was under the control of inspiratory pneumatic circuit and control loop 40 and control loop 40 retains the capacity to control mouth-pressure.

Performance-tests of a prototype system constructed in accordance with the present invention are illustrated in FIGS. 8–13. These tests were conducted using a Bio-Tek VT-2 test lung having a compliance range from 0.01 l/cm $H_2O$ to 0.15 l/cm $H_2O$ and a second order resistance range ($R_p'$) of from 0.002 cm $H_2O/(lpm)^2$ to 0.03 $H_2O/(lpm)^2$. The values of the inspiratory control function time constant ($t_1$), and the corresponding inspiratory digital coefficients, $A_i$ and $C_i$, were calculated on the basis of a nominal value for $C_p$ (50 ml/cm $H_2O$). Each of FIGS. 8–13 are plots of pressure (cm/$H_2O$ or hectopascals) versus time (secs.) and, in each case, the response of the system (actual mouth-pressure) is shown in response to a square wave input ($P_{in}$).

Figure 8:
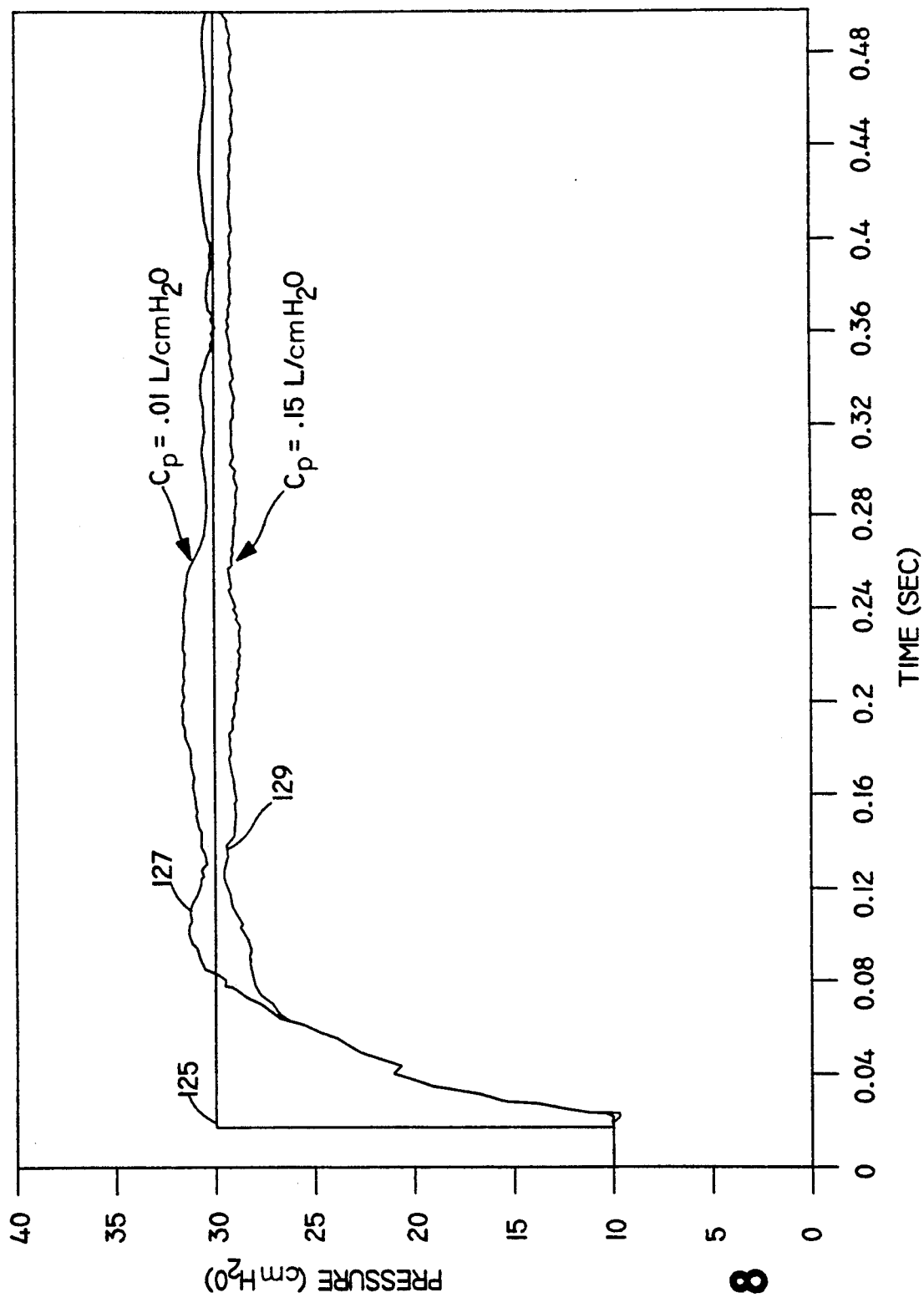
FIG. 8 is a plot of pressure vs. time showing the differences in response of a medical ventilator, constructed in accordance with the present invention, resulting from differences in the compliance of a patient's respiratory tract.

FIG. 8 shows the response of the system with the test lung's compliance set at minimum compliance (0.01 l/cm $H_2O$), curve 127, and the response of the system with the test lung's compliance set at maximum compliance (0.15 l/cm $H_2O$), curve 129. These curves show that system-response largely is unaffected by variations in lung-compliance and that the use of a nominal compliance to calculate $A_i$ and $C_i$ sacrifices little in system-performance. In each case, the one-sigma (63% of full scale) response time is less than 60 milliseconds, and the amount of resonance is less than 2 db. Of course, adjustments of $A_i$ and $C_i$ for variations in actual lung compliance will further enhance system-performance, and such adjustments are within the scope of the present invention. On the other hand, the system's performance is highly sensitive to patient to patient and flow-induced variations in $R_p$, as shown in FIG. 10 (discussed below).

Figure 9:
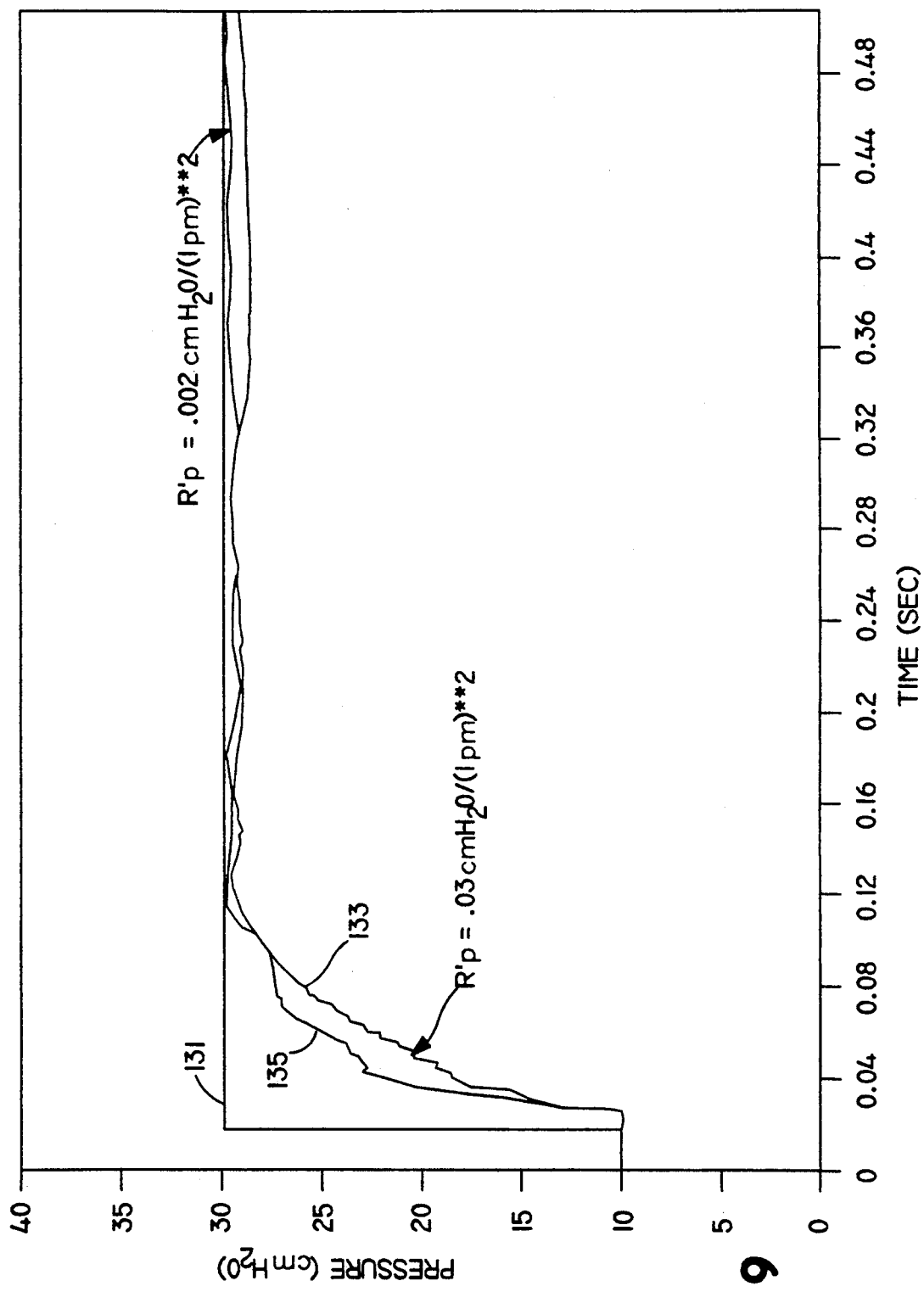
FIG. 9 is a plot of pressure vs. time showing the differences in response of a medical ventilator, constructed in accordance with the present invention, resulting from differences in the resistance of a patient's respiratory tract.

FIG. 9 shows the response of the system with the test lung's second order resistance $R_p'$ set at a minimum value (0.002 cm $H_2O/(lpm)^2$), curve 135, and the response of the system with the test lung's second order resistance set at a maximum value (0.03 cm $H_2O/(lpm)^2$), curve 133. In each case, after the inspiratory digital coefficients adjusted to reflect the actual value of $R_p'$, the one-sigma response time is less than 60 ms, and the degree of resonance is less than 2 db.

Figure 10:
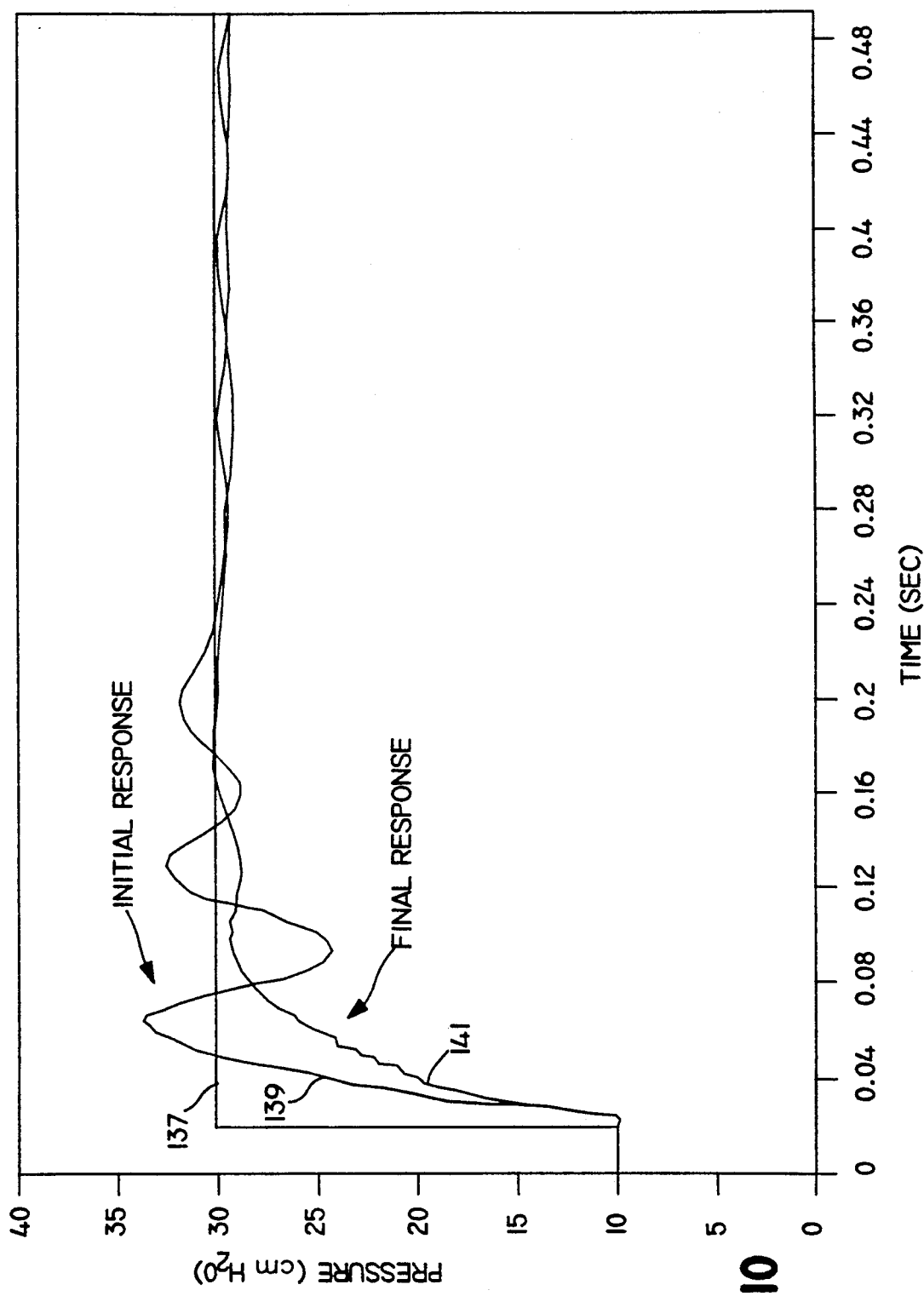
FIG. 10 is a plot of pressure vs. time showing the initial response of a medical ventilator, constructed in accordance with the present invention, resulting from an underestimation of the resistance of the patient's respiratory tract, and showing the ventilator's final response after adjustments for this underestimation.

FIG. 10, on the other hand, shows in curve 137 the response of the system before adjustment of the inspiratory digital coefficients to reflect the actual value of $R_p'$ and with the value of $R_p'$ used to calculate the initial inspiratory digital coefficients significantly below the actual value of $R_p'$. As a result, actual mouth pressure substantially overshoots desired mouth pressure, and significant oscillations occur. These oscillations, however, are damped by the system, and are not a safety concern. The response of the system several breaths later, after the inspiratory-control function has adjusted to reflect the actual value of $R_p'$, is shown in curve 141. This curve exhibits virtually no oscillation and has a one-sigma response time of less than 60 ms.

Figure 11:
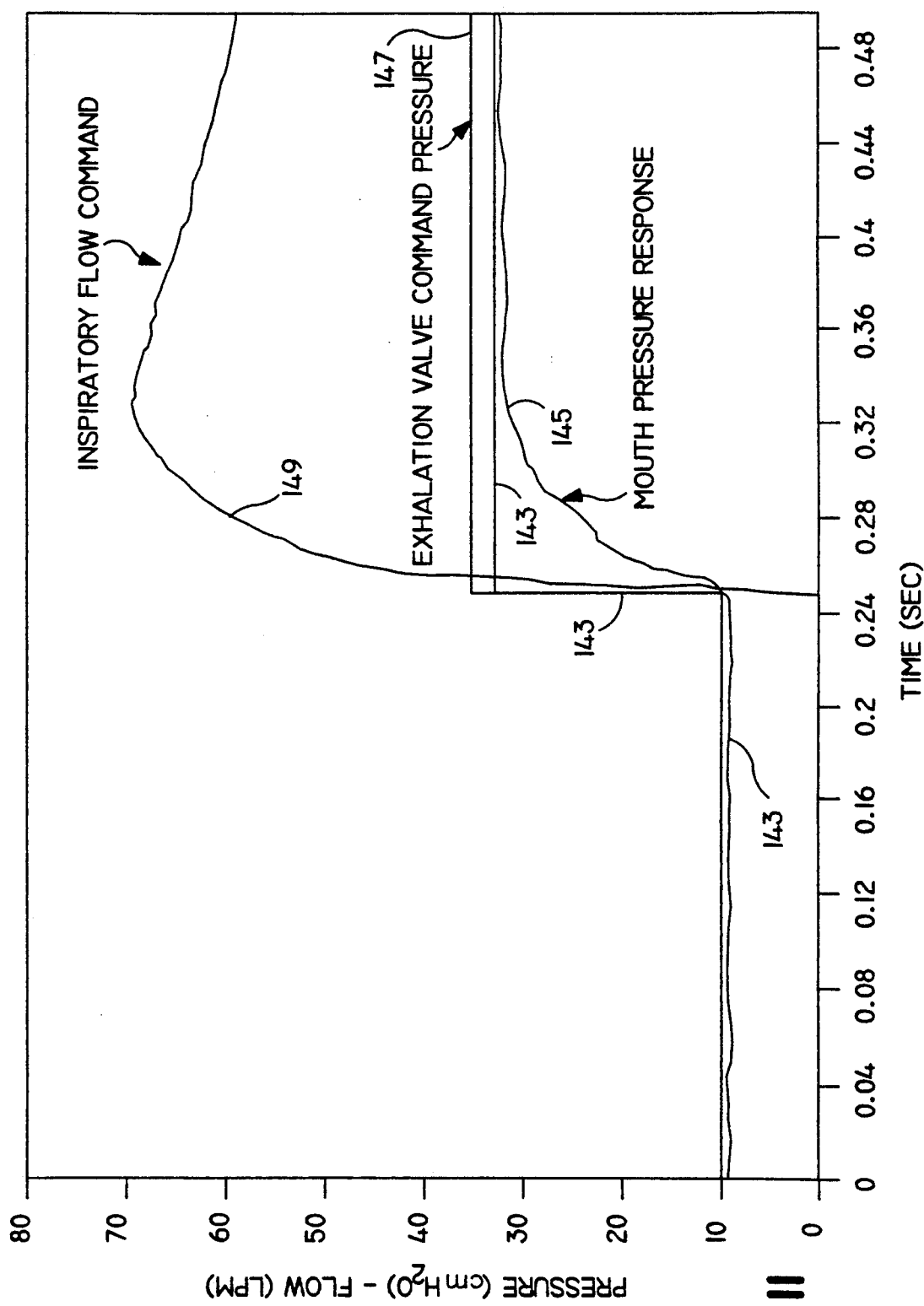
FIG. 11 is a plot of pressure vs. time showing the transfer from expiratory to inspiratory control by a medical ventilator, constructed in accordance with the present invention.
Figure 12:
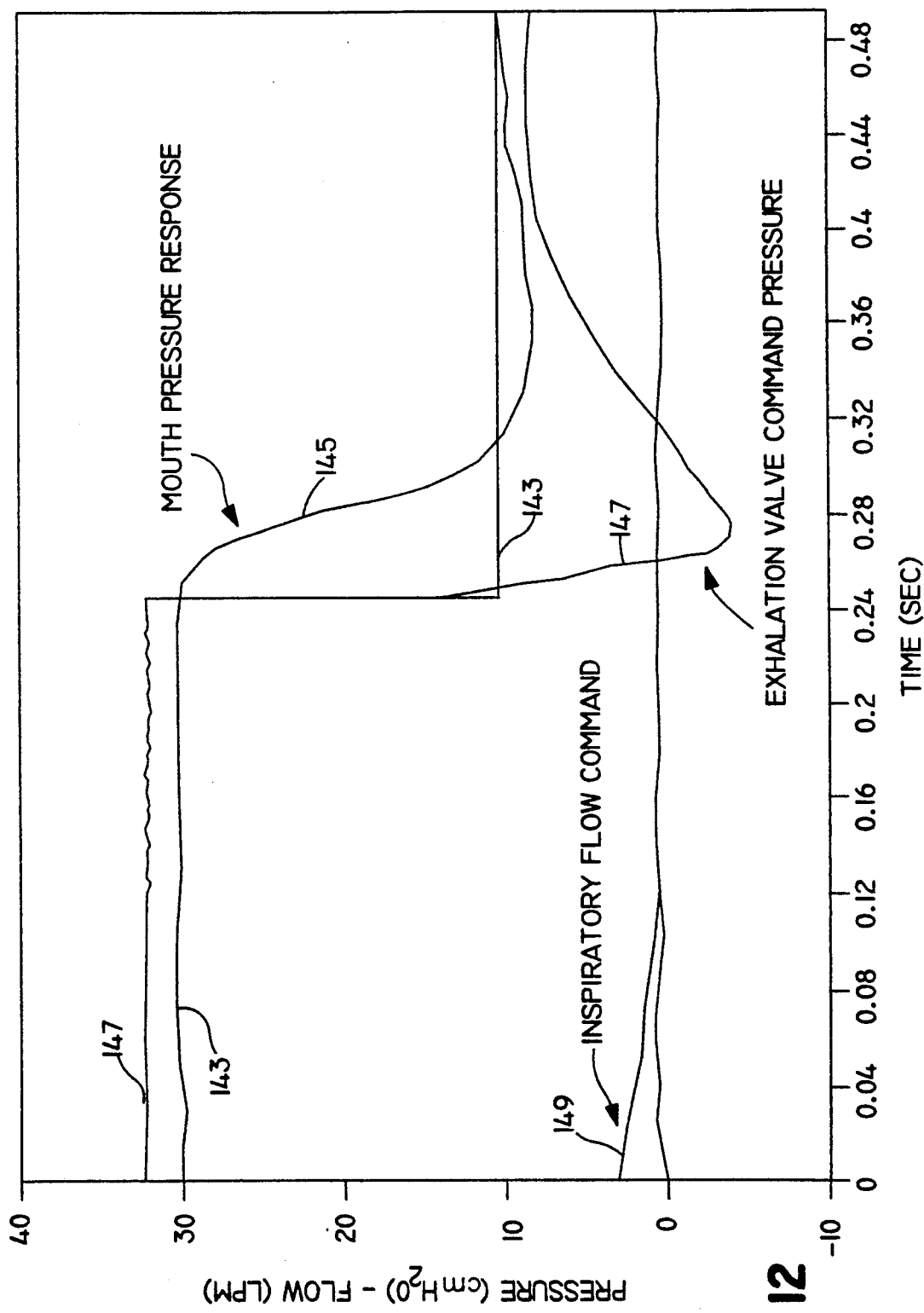
FIG. 12 is a plot of pressure vs. time showing the transfer from inspiratory to expiratory control by a medical ventilator, constructed in accordance with the present invention.

The operation of the synchronization algorithm is shown in FIGS. 11 and 12. Curve 149 is the output from the inspiratory-control function ($Q_{iv}$), curve 147 is the output from the second expiratory-control function ($P_{ec}$), curve 145 is the actual mouth-pressure, and curve 143 is $P_{in}$. From time zero to approximately time 0.24 secs., $P_{in}$ is low and mouth-pressure is under the control of expiratory pneumatic circuit and control loop 58. At approximately 0.24 secs., $P_{in}$ goes high terminating expiratory control, initiating control by inspiratory pneumatic circuit and control loop 40 and causing the value of $P_{ec}$ to be set to a value slightly higher than desired mouth pressure ($P_{in}+P_{off}$). The inspiratory flow command $Q_{iv}$ increases sharply to cause a corresponding sharp increase in actual mouth pressure to track $P_{in}$.

The transition from inspiratory back to expiratory control is shown in FIG. 12. At approximately 0.12 secs., while $P_{in}$ still is high, the value of $Q_{iv}$ goes to zero and control is transferred to the expiratory branch. Virtually no change initially occurs in the output from the second expiratory control function, however, because prior to $P_{in}$ going low, virtually no feedback error is present. On the other hand, at approximately 0.24 secs., $P_{in}$ goes low, the expiratory valve command pressure ($P_{ec}$) makes a sharp, negative step to a pressure less than 0 cm $H_2O$. Pressure control valve 9 and ejector valve 19 enable the application of this negative pressure to expiratory diaphragm valve 17. This negative pressure causes an immediate, corresponding sharp drop in actual mouth-pressure to cause actual mouth-pressure to track $P_{in}$. As actual mouth-pressure approaches the value of $P_{in}$, however, the expiratory valve command pressure begins to rise to prevent actual pressure from dropping below desired pressure.

Figure 13:
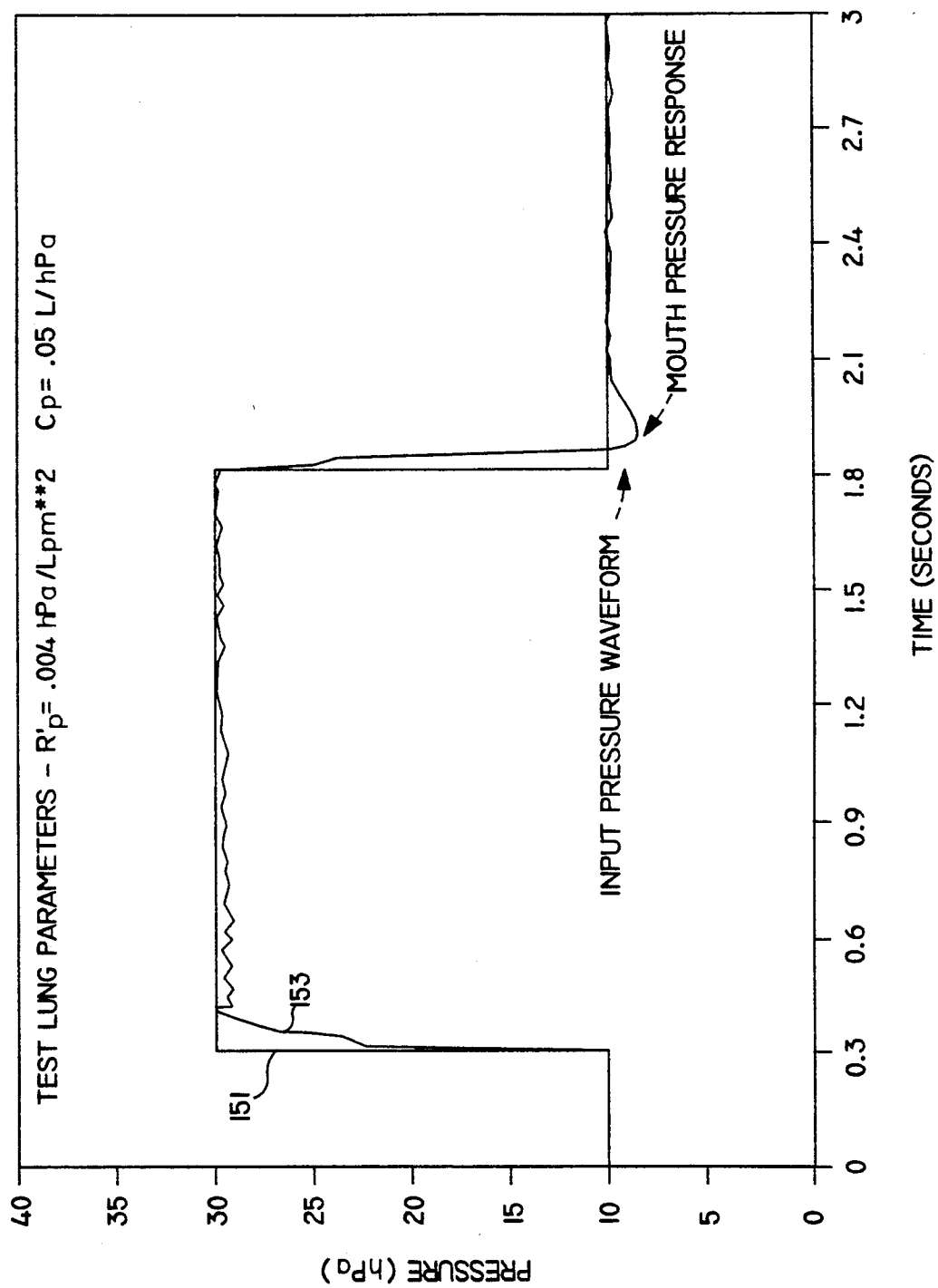
FIG. 13 is a plot of pressure vs. time showing a patient's mouth pressure, as controlled by a medical ventilator constructed in accordance with the present invention, in response to a square wave input at 20 breaths per minute.

FIG. 13 shows the steady state response of the prototype system in response to a square wave pressure input, curve 151, at 20 breadths per minute. The second order resistance ($R_p'$) and compliance ($C_p$) for the test lung were set at 0.004 hectopascals/(lpm)$^2$ and 0.05 l/hectopascal, respectively. Inspiratory and expiratory one-sigma response times are 30 ms and 36 ms, respectively, with virtually no resonance. Since a square wave input is the most difficult to track (being comprised of the most frequency components), this close tracking of desired pressure demonstrates the system's unique ability to cause actual pressure to track any desired input pressure waveform.

Finally, a prototype medical ventilator embodying the present invention was tested against a commercial, state-of-the-art medical ventilator, the Puritan-Bennett 7200A medical ventilator. These tests compared applicants' prototype ventilator against the Puritan-Bennett 7200A ventilator under identical conditions using a Bio-Tek VT-2 test lung. Both ventilators were operated in the constant-positive airway pressure (CPAP) and pressure-support (PSV) ventilatory modes over a wide range of conditions. The ventilators' performances were compared using five parameters:

(1) Work of Breathing (WOB): The deviation in WOB from that of an ideal machine operating in the particular ventilatory mode was measured. For example, the WOB for an ideal machine performing CPAP is zero.

(2) Expiratory Pressure Variation: The maximum positive pressure error observed during an exhalation was measured.

(3) Expiratory Response: Two measurements were made, the time required to achieve and maintain (including overshoots) both measurable and one-sigma levels of a negative direction pressure step.

(4) Inspiratory Pressure Variation: Analogous to expiratory pressure variation, the maximum negative pressure error observed during an inhalation was measured.

(5) Inspiratory Response: Analogous to expiratory response, two measurements were made, the time required to achieve and maintain (including overshoots) both measurable and one-sigma levels of a positive direction pressure step.

As measured by these parameters, the performance of applicants' prototype ventilator exceeded that of the Puritan-Bennett 7200A. For example, compared to the Puritan-Bennett ventilator, applicants' prototype ventilator, in the CPAP ventilatory mode, provided a 40% reduction in inspiratory WOB, a 75% reduction in expiratory WOB (combining to provide an overall 60% reduction in total WOB), a 55% reduction in inspiratory peak pressure errors, and a 45% reduction in peak expiratory pressure errors. In the PSV ventilatory mode, applicants, prototype ventilator, compared to the Puritan-Bennett ventilator, provided a 55% improvement in inspiratory response, a 75% improvement in expiratory response, a 60% reduction in inspiratory pressure variation, and a 70% reduction in expiratory pressure variation.

These objective tests were subjectively confirmed by users of both ventilators who observed a substantial improvement in breathing comfort, especially during respiratory phase transitions, in comparison to the Puritan-Bennett 7200A ventilator.

Although particular embodiments of the present invention have been shown and described, many varied embodiments incorporating the teachings of the present invention may be easily constructed by those skilled in the art. For example, pressure may be controlled at a point within the pneumatic circuit other than within, or closely adjacent to, the patient's mouth or respiratory tract. This point may be a chamber within a bellows assembly. Such a chamber would be present within the pneumatic circuit if, e.g., the medical ventilator were used for anesthesia ventilation. Also, rather than effect the various inspiratory and expiratory control functions using a digital microprocessor, discrete digital or analog components could be used.

We claim:

1. A medical ventilator for controlling the pressure of gas within a patient's respiratory tract, comprising:
   (a) a source of inspiratory gas;
   (b) an inspiratory conduit for directing the flow of said inspiratory gas from said source to said patient's mouth;
   (c) inspiratory flow-control means for controlling the flow of said inspiratory gas within said inspiratory conduit;
   (d) means for measuring the actual pressure of gas at a location such that the measurement is indicative of the actual pressure within said patient's respiratory tract;
   (e) first comparator means for comparing said actual pressure with a desired pressure and for generating a first error signal indicative of the difference between said actual pressure and said desired pressure;
   (f) processing means for processing said first error signal and for generating a first control-signal, in response to said first error signal, said processing means further comprising means for executing an inspiratory control function having a first time constant and for controlling said inspiratory flow-control means to cause said actual pressure to track said desired pressure; and
   (g) time-constant updating means for updating the value of said first time constant.

2. A medical ventilator as in claim 1, wherein said time-constant updating means comprises means for changing the value of said first time constant as a function of the magnitude of said first control signal.

3. A medical ventilator as in claim 2, wherein said time-constant updating means further comprises means for changing the value of said first time constant as a function of the resistance of said patient's respiratory tract.

4. A medical ventilator as in claim 3, wherein said time-constant updating means further comprises means for changing the value of said first time constant as a function of the compliance of said patient's respiratory tract.

5. A medical ventilator as in claim 1, wherein said time-constant updating means comprises means for changing the value of said first time constant as a function of the flow of said inspiratory gas within said inspiratory conduit.

6. A medical ventilator as in claim 1, wherein said time-constant updating means comprises means for changing the value of said first time constant as a function of the actual pressure of gas within said patient's mouth.

7. A medical ventilator as in claim 1, further comprising means for limiting the flow of said inspiratory gas from said source to that demanded by said patient.

8. A medical ventilator as in claim 1, wherein said source of inspiratory gas comprises a source of oxygen and a source of air.

9. A medical ventilator as in claim 8, wherein said inspiratory flow-control means comprises a first valve for controlling the flow of said oxygen and a second valve for controlling the flow of said air.

10. A medical ventilator as in claim 9, further comprising means for measuring the actual flow of said oxygen through said first valve, means for measuring the actual flow of said air through said second valve, means for determining the actual proportion of one of said flows to the total of both of said flows, and second comparator means for comparing said actual proportion with a desired proportion and for generating a second error signal indicative of the difference between said actual proportion and said desired proportion.

11. A medical ventilator as in claim 10, wherein said processing means further comprises means for processing said second error signal and for generating said first control signal in response to said first and second error signals such that said actual proportion tracks said desired proportion.

12. A medical ventilator as in claim 1, further comprising an expiratory conduit for directing the flow of expiratory gas from said patient's mouth, and an expiratory pressure-control means for controlling the pressure of said expiratory gas within said expiratory conduit.

13. A medical ventilator as in claim 12, wherein said processing means further comprises means for generating a second control signal, in response to said first error signal, for controlling said expiratory pressure-control means, said processing means executing an expiratory control function for causing said actual pressure to track said desired pressure.

14. A medical ventilator as in claim 13, further comprising synchronizing means for synchronizing said first and second control signals, said synchronizing means comprising evaluating means for evaluating, throughout the course of said patient's respiratory cycle, the capacity of said first control signal and said inspiratory flow-control means, and the capacity of said second control signal and said expiratory pressure-control means, for causing said actual pressure to track said desired pressure, and selecting means for selecting, on the basis of said evaluating, either said first control signal and said inspiratory flow-control means or said second control signal and said expiratory pressure-control means, for controlling said actual pressure.

15. A medical ventilator as in claim 13, wherein said expiratory pressure-control means comprises a diaphragm valve and a pressure-regulating valve for applying back pressure to said diaphragm valve.

16. A medical ventilator as in claim 15, further comprising means for applying a negative back pressure to said diaphragm valve.

17. A medical ventilator as in claim 16, wherein said means for applying a negative back pressure comprises a venturi.

18. A medical ventilator as in claim 15, further comprising means, within said expiratory conduit and downstream from said diaphragm valve, for creating a pressure below that of the surrounding atmosphere.

19. A medical ventilator as in claim 1, wherein said first comparator means, said processing means and said time-constant updating means comprise a digital microprocessor.

20. A medical ventilator as in claim 1, wherein said inspiratory conduit comprises a wye piece adjacent said patient's mouth, and said means for measuring is located within said wye piece.

21. A medical ventilator as in claim 1, wherein said means for measuring is located within said patient's mouth.

22. A medical ventilator for providing closed loop control of the pressure of gas within a patient's mouth, comprising:
 (a) a source of inspiratory gas;
 (b) inspiratory means for transmitting said inspiratory gas to the mouth of said patient;
 (c) means for generating the actual pressure of gas at location such that the measurement is indicative of the actual pressure within said patient's mouth;
 (d) a processor, said processor comprising first comparator means for comparing said actual pressure with a desired pressure and for generating a first error signal indicative of the difference between said actual pressure and said desired pressure, said processor further comprising an adaptive feedback controller means for processing said first error signal in accordance with a first set of processing parameters and for controlling said inspiratory means such that said actual pressure tracks said desired pressure, and said processor further comprising means for updated said processing parameters during the course of said patient's respiratory cycle.

23. A medical ventilator as in claim 22, further comprising means for varying said desired pressure in accordance with a selected function of time.

24. A medical ventilator as in claim 22, further comprising means for converting said first error signal to a digital value, and wherein said processor comprises a digital microprocessor, and said first set of processing parameters comprise a set of digital coefficients for multiplying said digital value.

25. A medical ventilator as in claim 22, wherein said processing parameters are a function of the resistance and compliance of said patient's respiratory tract, and wherein said processor further comprises means for periodically determining the value of said processing parameters as a function of said resistance and of the flow of said inspiratory gas into said mouth.

26. A medical ventilator as in claim 25, further comprising means for periodically determining the value of said resistance as a function of the flow of said inspiratory gas into said mouth and said actual pressure.

27. A medical ventilator as in claim 22, further comprising expiratory means for transmitting expiratory gas from the mouth of said patient, and wherein said adaptive controller further comprises means for controlling said expiratory means such that said actual pressure tracks said desired pressure.

28. A medical ventilator as in claim 27, wherein said means for controlling said expiratory means comprises means for processing said first error signal in accordance with a second set of processing parameters.

29. A medical ventilator as in claim 28, wherein said adaptive controller further comprises means for generating a first control signal for controlling said inspiratory means, means for generating a second control signal for controlling said expiratory means, and selecting means for selecting either said first control signal and said inspiratory means, or said second control signal and said expiratory means, for causing said actual pressure to track said desired pressure.

30. A medical ventilator as in claim 29, wherein said adaptive controller further comprises evaluating means for evaluating the capacity of said inspiratory means and said expiratory means for causing said actual pressure to track said desired pressure, and means for setting said first control signal to a predetermined value during periods when said inspiratory means lacks the capacity to cause said actual pressure to track said desired pressure, and for setting said second control signal to a predetermined value during periods when said expiratory means lacks the capacity for causing said actual pressure to track said desired pressure.

31. A medical ventilator as in claim 27, wherein said expiratory means comprises an expiratory conduit for directing the flow of expiratory gas from said mouth, a diaphragm valve for controlling the flow of said expiratory gas, and means for applying back pressure to said diaphragm valve.

32. A medical ventilator as in claim 31, wherein said means for applying back pressure to said diaphragm valve comprises means for applying a negative back pressure.

33. A medical ventilator as in claim 32, wherein said means for applying a negative back pressure comprises a venturi.

34. A medical ventilator as in claim 31, further comprising means, within said expiratory conduit and downstream of said diaphragm valve, for creating a pressure below that of the surrounding atmosphere.

35. A medical ventilator as in claim 30, wherein said adaptive controller further comprises means for causing, throughout the course of said patient's respiratory cycle, one of said first and second control signals to be set to a predetermined value.

36. A medical ventilator for providing continuous, closed loop control of the pressure of gas within a patient's mouth, comprising:
 (a) a source of inspiratory gas;
 (b) inspiratory means for transmitting said inspiratory gas to the mouth of said patient;
 (c) expiratory means for transmitting expiratory gas from the mouth of said patient;
 (d) means for measuring the actual pressure of gas at a location such that the measurement is indicative of the actual pressure within said patient's mouth;
 (e) comparator means for comparing said actual pressure with a desired pressure and for generating an error signal indicative of the difference between said actual pressure and said desired pressure;
 (f) a control system for processing said error signal in accordance with a first set of processing parameters and for generating a first control signal for controlling said inspiratory means, and for processing said error signal in accordance with a second set of processing parameters and for generating a second control signal for controlling said expiratory means;
 (g) evaluating means for evaluating the capacity of said first control signal and said inspiratory means, and the capacity of said second control signal and said expiratory means, for causing said actual pressure to track said desired pressure; and
 (h) selecting means for selecting, on the basis of said evaluating, either said first control signal and said inspiratory means, or said second control signal and said expiratory means, for controlling said actual pressure.

37. A medical ventilator as in claim 36, further comprising means for setting said first control signal to a predetermined value during periods when said inspiratory means lacks the capacity for causing said actual pressure to track said desired pressure, and for setting said second control signal to a predetermined value during periods when said expiratory means lacks the capacity for causing said actual pressure to track said desired pressure.

38. A medical ventilator as in claim 37, further comprising means for causing, during the course of said patient's respiratory cycle, one of said first and second control signals to be set to a predetermined value.

39. A medical ventilator as in claim 37, further comprising means for prohibiting said inspiratory means from transmitting inspiratory gas when said first control signal is set to a predetermined value, and means for prohibiting said expiratory means from transmitting expiratory gas when said second control signal is set to a predetermined value.

40. A medical ventilator as in claim 39, wherein said expiratory means comprises a diaphragm valve for controlling the flow of said expiratory gas and means for applying back pressure to said diaphragm valve, and wherein said means for prohibiting said expiratory means from transmitting comprises means for setting said back pressure to a predetermined incremental pressure plus said desired pressure.

41. A medical ventilator as in claim 36, wherein said control system comprises means for changing said first set of processing parameters during the course of said patient's respiratory cycle.

42. A medical ventilator as in claim 41, wherein said means for changing comprises means for determining the value of said first set of processing parameters as a function of the resistance of said patient's respiratory tract and the flow of said inspiratory gas into said patient's mouth.

43. A medical ventilator as in claim 36, wherein said comparator means, said control system, said evaluating means and said selecting means comprise a microprocessor.

44. A system for providing closed loop control of the pressure of gas within a patient's mouth, comprising:
 (a) an expiratory conduit for directing the flow of expiratory gas from said mouth;
 (b) a diaphragm valve for controlling the flow of said expiratory gas within said expiratory conduit;
 (c) pressure means for applying both positive and negative back pressure to said diaphragm valve, said pressure means comprising a pressure-regulating solenoid valve and a venturi, said pressure means further comprising means for establishing a reference pressure for said pressure-regulating solenoid valve below that of the surrounding atmosphere;
 (d) means for measuring the actual pressure of gas at a location such that the measurement is indicative of the actual pressure within said mouth;
 (e) comparator means for comparing said actual pressure with a desired pressure and for generating an error signal indicative of the difference between said actual pressure and said desired pressure; and
 (f) a control system for processing said error signal in accordance with a first set of processing parameters and for generating a first control signal for controlling said pressure means such that said actual pressure tracks said desired pressure.

45. A system as in claim 44, further comprising means, within said expiratory conduit and downstream of said diaphragm valve, for creating a pressure below that of the surrounding atmosphere.

46. A system as in claim 44, further comprising means for measuring the actual back pressure applied to said diaphragm valve, second comparator means for comparing said actual back pressure with a desired back pressure and for generating a second error signal indicative of the difference between said actual back pressure and said desired back pressure, and wherein said control system comprises means for processing said second error signal in accordance with a second set of processing parameters for generating said first control signal.

47. A system for providing closed loop control of the pressure of gas within a patient's mouth, comprising:
 (a) an expiratory conduit for directing the flow of expiratory gas from said mouth;

(b) a diaphragm valve for controlling the pressure of said expiratory gas within said expiratory conduit;
(c) pressure means for applying back pressure to said diaphragm valve;
(d) means for measuring the actual pressure of gas at a location such that the measurement is indicative of the actual pressure within said mouth;
(e) first comparator means for comparing said actual pressure with a desired pressure and for generating a first error signal indicative of the difference between said actual pressure and said desired pressure;
(f) first processing means for processing said first error signal in accordance with a first set of processing parameters and for generating a first control signal;
(g) means for measuring the actual back pressure applied to said diaphragm valve;
(h) second comparator means for comparing the magnitude of said first control signal with said actual back pressure and for generating a second error signal indicative of the difference between said actual back pressure and the magnitude of said first control signal; and
(i) second processing means for processing said second error signal in accordance with a second set of processing parameters and for generating a second control signal for controlling said pressure means such that said actual pressure of gas within said mouth tracks said desired pressure.

48. A system as in claim 47, wherein said first and second processing means comprise a digital microprocessor.

49. A system as in claim 47, wherein said pressure means comprises means for applying both positive and negative back pressure to said diaphragm valve.

50. A medical ventilator as in claim 49, wherein said pressure means comprises a pressure-regulating solenoid valve and a venturi for establishing a reference pressure for said pressure-regulating solenoid valve below that of the surrounding atmosphere.

51. A system as in claim 50, further comprising means, within said expiratory conduit and downstream of said diaphragm valve, for creating a pressure below that of the surrounding atmosphere.

52. A control system for providing closed loop control of the pressure of gas within a patient's mouth, comprising:
(a) inspiratory means for transmitting inspiratory gas to the mouth of said patient;
(b) means for measuring the actual pressure of gas at a location such that the measurement is indicative of the actual pressure within said patient's mouth;
(c) comparator means for comparing said actual pressure with a desired pressure and for generating an error signal indicative of the difference between said actual pressure and said desired pressure;
(d) an adaptive controller means for processing said error signal in accordance with a set of processing parameters and for generating a first control signal for controlling said inspiratory means such that said actual pressure tracks said desired pressure; and
(e) means for changing the value of said processing parameters as a function of the magnitude of said first control signal.

53. A medical ventilator as in claim 52, further comprising expiratory means for transmitting expiratory gas from the mouth of said patient, and wherein said adaptive controller further comprises means for processing said error signal in accordance with a second set of processing parameters and for generating a second control signal for controlling said expiratory means such that said actual pressure tracks said desired pressure.

54. A medical ventilator as in claim 52, wherein said means for changing further comprise means for changing the value of said processing parameters as a function of the resistance of said patient's respiratory tract.

55. A method for controlling the pressure of gas within a patient's respiratory tract, comprising:
(a) providing a source of inspiratory gas;
(b) directing a flow of said inspiratory gas from said source to said patient's mouth;
(c) measuring the actual pressure of gas at a location such that the measurement is indicative of the actual pressure within said patient's respiratory tract;
(d) comparing said actual pressure with a desired pressure and generating an error signal indicative of the difference between said actual pressure and said desired pressure;
(e) processing said error signal in accordance with a set of processing parameters and generating a control signal for controlling said directing such that said actual pressure tracks said desired pressure; and
(f) adjusting the value of said processing parameters as a function of the flow of inspiratory gas into said patient's mouth.

56. A method as in claim 55, further comprising the step of adjusting the value of said processing parameters as a function of the resistance of said patient's respiratory tract.

57. A method as in claim 56, further comprising the step of adjusting the value of said processing parameters as a function of the compliance of said patient's respiratory tract.

58. A method for providing continuous, closed loop control of the pressure of gas within a patient's mouth throughout the patient's respiratory cycle, comprising:
(a) providing a source of inspiratory gas;
(b) transmitting said inspiratory gas to the mouth of said patient;
(c) directing expiratory gas from the mouth of said patient;
(d) measuring the actual pressure of gas at a location such that the measurement is indicative of the actual pressure within said patient's mouth;
(e) comparing said actual pressure with a desired pressure and generating an error signal indicative of the difference between said actual pressure and said desired pressure;
(f) processing said error signal in accordance with a first set of processing parameters and generating a first control signal for controlling said transmitting;
(g) processing said error signal in accordance with a second set of processing parameters and generating a second control signal for controlling said directing;
(h) evaluating the capacity of said first control signal and said transmitting, and the capacity of said second control signal and said directing, for causing said actual pressure to track said desired pressure; and
(i) selecting, on the basis of said evaluating, either said first control signal and said transmitting, or said second control signal and said directing, for controlling said actual pressure.

59. A method as in claim 58, further comprising the step of changing said first set of processing parameters as a function of the flow of gas into said patient's mouth.

* * * * *